US012758254B2

(12) United States Patent
Hu et al.

(10) Patent No.: US 12,758,254 B2
(45) Date of Patent: *Oct. 13, 2026

(54) PUNCTURE SYSTEM

(71) Applicant: BEIJING MEDIS MEDICAL TECHNOLOGY CO., LTD., Beijing (CN)

(72) Inventors: Meng Hu, Beijing (CN); Dong Guo, Beijing (CN)

(73) Assignee: BEIJING MEDIS MEDICAL TECHNOLOGY CO., LTD., Beijing (CN)

( * ) Notice: Subject to any disclaimer, the term of this patent is extended or adjusted under 35 U.S.C. 154(b) by 236 days.

This patent is subject to a terminal disclaimer.

(21) Appl. No.: 18/293,465

(22) PCT Filed: Jul. 29, 2022

(86) PCT No.: PCT/CN2022/108987

§ 371 (c)(1),
(2) Date: Jul. 5, 2024

(87) PCT Pub. No.: WO2023/006072

PCT Pub. Date: Feb. 2, 2023

(65) Prior Publication Data

US 2025/0032151 A1 Jan. 30, 2025

(30) Foreign Application Priority Data

Jul. 30, 2021 (CN) ........................ 202110869305.6

(51) Int. Cl.
*A61B 17/34* (2006.01)
*A61M 25/06* (2006.01)

(52) U.S. Cl.
CPC ..... *A61B 17/3403* (2013.01); *A61M 25/0662* (2013.01); *A61B 2017/3413* (2013.01); *A61M 2025/0681* (2013.01)

(58) Field of Classification Search
CPC ...... A61M 25/0606; A61M 2025/0681; A61M 25/065; A61B 17/3403; A61B 10/0233;
(Continued)

(56) References Cited

U.S. PATENT DOCUMENTS 6,216,029 B1 4/2001 Paltieli
8,632,468 B2 1/2014 Glossop et al.
(Continued)

FOREIGN PATENT DOCUMENTS

CN 102266250 A 12/2011
CN 102395327 A 3/2012
(Continued)

OTHER PUBLICATIONS

European Patent Office, "Communication Pursuant to Rule 154(1) EPC" issued in connection with EP Patent Application No. 22848676.7 on Feb. 27, 2025, 14 pages.
(Continued)

*Primary Examiner* — Brooke Lyn Klein
(74) *Attorney, Agent, or Firm* — Hanley, Flight & Zimmerman, LLC

(57) ABSTRACT

A puncture system, which utilizes intervention navigation technology and a corresponding puncture instrument to operate puncture surgery that features easier operation, higher accuracy and effectiveness, improved safety, and fewer complications, and that has no blind zones during surgery monitoring.

10 Claims, 16 Drawing Sheets

(58) Field of Classification Search
CPC .............. A61B 10/025; A61B 10/0241; A61B 10/0266; A61B 10/0275; A61B 10/0283; A61B 2010/045; A61B 8/0841
See application file for complete search history.

(56) References Cited

U.S. PATENT DOCUMENTS

| | | | | |
|---|---|---|---|---|
| 2009/0275833 | A1 | 11/2009 | Ikeda et al. | |
| 2010/0217117 | A1* | 8/2010 | Glossop | A61B 34/20 600/424 |
| 2010/0298704 | A1 | 11/2010 | Pelissier et al. | |
| 2010/0298705 | A1* | 11/2010 | Pelissier | A61B 8/4254 600/443 |
| 2012/0143029 | A1 | 6/2012 | Silverstein et al. | |
| 2014/0046261 | A1 | 2/2014 | Newman et al. | |
| 2015/0201911 | A1 | 7/2015 | Halmann et al. | |
| 2018/0000446 | A1 | 1/2018 | Lu et al. | |
| 2019/0307516 | A1 | 10/2019 | Schotzko et al. | |
| 2019/0307518 | A1* | 10/2019 | Schotzko | G16H 30/40 |
| 2020/0214739 | A1 | 7/2020 | Shi | |
| 2022/0175416 | A1* | 6/2022 | Ebnet | A61M 25/0606 |
| 2022/0218316 | A1* | 7/2022 | Ries | A61B 90/06 |

FOREIGN PATENT DOCUMENTS

| | | | |
|---|---|---|---|
| CN | 103006261 | A | 4/2013 |
| CN | 103027712 | A | 4/2013 |
| CN | 106821499 | A | 6/2017 |
| CN | 108210024 | A | 6/2018 |
| CN | 109259827 | A | 1/2019 |
| CN | 109512473 | A | 3/2019 |
| CN | 209153768 | U | 7/2019 |
| CN | 110279467 | A | 9/2019 |
| CN | 112040875 | A | 12/2020 |
| CN | 113456189 | A | 10/2021 |
| CN | 216754558 | U | 6/2022 |

OTHER PUBLICATIONS

China National Intellectual Property Administration, "First Notification of Office Action," issued in connection with Chinese Patent Application No. 202110869305.6, dated Aug. 10, 2024, 8 pages. [English translation provided].

China National Intellectual Property Administration, "First Search Report," issued in connection with Chinese Patent Application No. 202110869305.6, dated Aug. 10, 2024, 4 pages. [English translation provided].

International Searching Authority, "Written Opinion of the International Searching Authority," issued in connection with International Application No. PCT/CN2022/108987, mailed on Oct. 28, 2022, 13 pages [English Translation Included].

International Searching Authority, "International Preliminary Report on Patentability," issued in connection with International Application No. PCT/CN2022/108987, mailed on Oct. 28, 2022, 15 pages [English Translation Included].

International Searching Authority, "International Search Report," issued in connection with International Application No. PCT/CN2022/108987, mailed on Oct. 28, 2022, 3 pages.

European Patent Office, "Extended European Search Report" issued on Jul. 2, 2025 for counterpart European Patent Application No. 22848676.7, 15 pages.

* cited by examiner

PUNCTURE SYSTEM

CROSS-REFERENCE TO RELATED APPLICATIONS

This patent arises from a U.S. National Stage of International Application No. PCT/CN2022/108987 filed on Jul. 29, 2022, which claims priority to Chinese Patent Application No. 202110869305.6 which was filed on Jul. 30, 2021. Both International Application No. PCT/CN2022/108987 and Chinese Patent Application No. 202110869305.6 are hereby incorporated by reference in their entireties.

TECHNICAL FIELD

The present disclosure relates to the technical field of medical devices, and in particular to a puncture system.

BACKGROUND

Hereinafter the relevant background art of the present disclosure is illustrated, but these illustrations do not necessarily constitute the prior art of the present disclosure.

Interventional Radiology is a marginal discipline that developed rapidly in the late 1970s. It includes a series of techniques of diagnosis and treatment of various diseases by using instruments such as catheters, guide wires and the like under the guidance of medical imaging equipment, based on image diagnostics and clinical diagnostics, and combined with the principle of clinical therapeutics. That is, it is a discipline that a specially-made catheter or instrument is inserted into a site of lesion for diagnostic imaging and treatment by a transdermal puncture approach or original orifices of the human body under the guidance of imaging medicine (X-ray, ultrasound, CT (Computed Tomography), MRI (Magnetic Resonance Imaging)), or the tissues are collected for examinations of the cytology, the bacteriology and the biochemistry.

Interventional radiology provides new drug delivery route and surgical method for modern medical diagnosis and treatment. Compared with traditional drug delivery routes and surgical methods, the interventional radiology is more direct, effective, simple and microtraumatic. The interventional radiology has opened up a new way of treatment, and it is simple, safe, with less trauma, with fewer complications, quick effect, and microtraumatic; has strong repeatability, accurate positioning, high curative effect and quick effect; has a low comorbidity rate. The application of various technologies is simple and easy.

The interventional radiology may be divided into interventional diagnosis and interventional therapy according to the purpose; and may be divided into vascular interventional radiology (drug perfusion; embolization technique; angioplasty and stenting; filter technology, etc.) and non-vascular radiological interventionology (puncture biopsy; drainage technology; removal of foreign bodies; lumen stent, etc.) according to the technology; and may be divided into tumor interventional radiology, non-tumor interventional radiology, neurointerventional radiology and so on according to the scope of clinical application.

Medical imaging equipment used in the interventional radiology mainly includes X-ray, ultrasound, CT, MRI, etc., among which, X-ray and CT have radioactivity, but MRI has to be applied in conjunction with non-ferromagnetic devices and environments. For intraoperative interventional guidance, multiple number of times of imaging and long-time imaging is required, harm to patients and health care workers caused by the radioactivity of X-ray and CT as well as the non-ferromagnetic requirement of MRI for supporting equipment and environment both of which cause inconvenience and difficulty for interventional diagnosis and treatment, which hinders the clinical application of interventional radiology.

Ultrasound has the characteristics of real-time imaging and no radioactivity and thus has been widely used in interventional radiology. However, the non-intuitive two-dimensional nature of ultrasonic imaging, and the coplanar nature of an ultrasonic imaging plane and an interventional tool and other similar problems may easily lead to difficulties and mistakes in positioning and guiding the interventional tool, and in turn lead to puncture errors, trauma, complications and other conditions, which thus requires the medical staff for executing intervention diagnosis and treatment to have a large amount of training, skillful technique and rich experience.

Ultrasonic interventional navigation is an important means of interventional radiology, which can display the movement of the interventional tool in the tissue in real time and provide a basis for selection of an interventional path. However, conventional ultrasound-guided intervention relies heavily on the operator's skill, experience and ultrasonic instrument performance, and may have problems such as many times of intervention and long operation time and the like, which may lead to an increased incidence of complications.

Due to the characteristics of ultrasonic imaging, in order to perform real-time imaging navigation of interventional instruments during the interventional process, it is necessary to keep the target, interventional instrument and ultrasonic imaging plane in the same plane. Due to the small tissue density, displacement/deformation is easy to happen under pressure, it necessary to readjust the angle of the ultrasonic probe and strength of pressing at any time according to the situation, and often the position of the corresponding interventional instrument will also change, then it is necessary to adjust the ultrasonic probe and the interventional instrument at the same time to re-image navigation, which is very difficult and has very high requirements for doctors.

Due to the volume effect of ultrasound, the imaging of the interventional instrument by ultrasonic equipment cannot reflect its true position and size, thus affecting the accuracy of navigation.

Interventional radiology has a wide range of clinical applications, which may be applied to vascular diseases (such as vascular stenosis, portal hypertension, etc.), heart diseases (mitral stenosis, coronary artery stenosis, etc.), tumors (tumor blood supply artery infusion chemotherapy, embolization treatment of malignant tumors, etc.), non-vascular diseases (digestive tract, urinary tract, biliary tract, airway, stenosis of naso-lacrimal duct, etc.), puncture biopsy, etc.

Among them, the interventional diagnosis and treatment in which the intervention pathway is narrow and tortuous, has angle requirements, and needs to pass through important tissues and organs, such as transjugular intrahepatic portosystemic shunt (TIPS), has a high degree of difficulty, a high risk factor and high skill requirements, and in particular needs accurate and effective navigation techniques.

TIPS derives from the fact that the portal vein is often punctured during transjugular vein cholangiography and transhepatic biopsy, and is developed by renowned interventional radiologist Rosch J and his colleagues. By establishing a shunt inside the liver parenchyma between the hepatic vein and the portal vein, the portal vein resistance can be significantly reduced structurally in a microtraumatic manner, and this is one of the key measures to reduce portal vein pressure in patients with cirrhosis.

Since the first truly clinically significant TIPS with metal stent was performed in January 1988, through continuous improvement, at present, TIPS has been widely used in the treatment of esophageal and gastric varices rupture and bleeding, intractable hydrothorax and ascites, Budd-Chiari syndrome (BCS) and liver sinusoidal obstruction syndrome and the like caused by portal hypertension in cirrhosis (De Franchis, R. and V. I. F. Baveno, Expanding consensus in portal hypertension: Report of the Baveno VI Consensus Workshop: Stratifying risk and individualizing care for portal hypertension. J Hepartol, 2015.63 (3): p. 743-52) (Chinese Medical Doctor Association Branch of Interventional Physicians. Chinese College of Interventionalists (CCI) clinical practice guidelines: management of TIPS for portal hypertension [J]. Chinese Journal of Hepatology, 2018, 27 (8): 582-593).

The operation process of TIPS technology is as follows: 1) anesthesia; 2) portal vein imaging; 3) internal jugular vein puncture; 4) hepatic vein intubation; 5) portal vein puncture; 6) portal cavity channel establishment; 7) balloon catheter dilation and endoluminal stent implantation; 8) measurement and optimal threshold of PPG postoperatively; 9) embolization of portal collateral vessels.

Indications for TIPS include: 1) acute esophageal varix and bleed; 2) gastric varix and bleed; 3) preventing esophageal varix and bleed; 4) preventing gastric varix and bleed; 5) cirrhotic recalcitrant or recurrent ascites; hepatic pleural fluid and hepatorenal syndrome; 6) BCS (Budd-Chiari syndrome); 7) hepatic sinus obstruction syndrome; 8) portal hypertension complicated with portal vein thrombosis;

Contraindications for TIPS include:

1. Absolute contraindications: (1) congestive heart failure or severe valvular cardiac insufficiency; (2) uncontrollable systemic infection or inflammation; (3) Child-Pugh score>13 or end-stage liver disease score>18; (4) severe pulmonary hypertension; (5) severe renal insufficiency (except hepatogenic renal insufficiency); (6) rapidly progressive liver failure; (7) diffuse malignant tumor of liver; (8) contrast agent hypersensitivity.
2. Relative contraindications: (1) congenital cystic dilatation of intrahepatic bile duct (*Caroli* disease), obstructive dilatation of bile duct; (2) polycystic liver disease; (3) cavernous transformation of the portal vein; (4) moderate pulmonary hypertension; (5) severe or refractory HE (hepatic encephalopathy); (6) bilirubin>51.3 μmol/L (except cholestatic cirrhosis); (7) severe coagulation disease.

At present, there are three main technical difficulties in TIPS: 1) The success rate of portal vein puncture is low under X-ray monitoring; 2) Postoperative portal shunt channel restenosis; 3) The incidence of postoperative hepatic encephalopathy (HE) is high.

At present, with the use of PTFE (Polytetrafluoroethylene) coated stents (Perarnau J M, Le Gouge A, Nicolas C, et al. Covered vs. uncovered stents for transjugular intrahepatic portosystemic shunt: a randomized controlledtrial [J]. J Hepatol, 2014, 60 (5): 962-968. DOI: 10.1016/j.jhep.2014.01.015.) and special ePTFE (expended polytetrafluoroethylene) coated stents (Charon. J P, Alaeddin F H, Pimpalwar S A, et al. Results of aretrospective muhicenter trial of the Viatorr expanded Polyetrafluoroethylene covered stent—graft for transjugular intrahepatic portosystemic shunt creation [J]. JVIR (Journal of Vascular and Interventional Radiology), 2004, 15:1219. 1230.), the shunt stenosis rate of subjects has been significantly reduced. The incidence of HE after TIPS is 18% to 45%. A retrospective clinical study on the establishment of shunt channels at the position of left branch of portal vein finds that the incidence of HE can be reduced to a certain extent (Zhu Qingliang, Deng Mingming, Tang Shixiao, et al. Effect of different stent positions on the incidence of hepatic encephalopathy after TIPS. Contemporary Medicine, 2016, 22 (4): 92-93.), and clinical studies on the selection of stents with smaller diameters and intrastent flow restriction finds that the incidence of HE is reduced to a certain extent and the symptoms of most patients with HE are improved (Riggio, O. et al. J Hepatol, 2010, 53 (2): p. 267-72) (Chinese Medical Doctor Association Branch of Interventional Physicians. Chinese clinical practice guidelines for portal hypertension transjugular intrahepatic portal shunt [J]. Chinese Journal of Hepatology, 2018, 27 (8): 582-593).

Therefore, it has become an urgent problem to solve the monitoring blind zone, real-time monitoring and guiding the puncture instrument to the predetermined position of the portal vein through hepatic venipuncture safely and effectively, and reducing complications, through the puncture navigation technology.

In the process of transhepatic vein puncture of the portal vein during TIPS, the complications related to the technique mainly include biliary tract bleeding and injury, abdominal hemorrhage, hepatic artery injury, bile peritonitis, skin radiation burn and hematoma at the puncture site (Darishina S R, Haskal Z J, Midia M, et al. Quality improvement guidelines for transjugular intrahepatic portosystemic shunts. J Vasc Interv Radiol 2016; 27 (1): 1-7.). Although the incidence of these complications can be further reduced with the promotion of TIPS technology and the accumulation of operator experience, transhepatic vein puncture of the portal vein is still the biggest technical difficulty during TIPS surgery, the key step for the success or failure of TIPS, and the operation link that is prone to serious complications (Chinese Medical Doctor Association Branch of Interventional Physicians. Chinese clinical practice guidelines for portal hypertension transjugular intrahepatic portal shunt [J]. Chinese Journal of Hepatology, 2018, 27 (8): 582-593).

The general procedure of transhepatic vein puncture of the portal vein is as follows: the operator estimates the puncture angle by observing imaging data before surgery; the patient underwent local anesthesia in the catheter room; first, puncturing the right internal jugular vein; sending the catheter from the right internal jugular vein, through the right atrium and inferior vena cava to the right internal hepatic vein with the aid of X-ray fluoroscopy; performing the portal vein 15 cuneiform angiography to clarify the structure of the portal vein and its branch anatomy; and puncturing the portal vein from the right hepatic vein forward and down.

This is currently considered the safest puncture route for TIPS surgery (Siramolpiwat, S., World J Gastroenterol, 2014. 20 (45): p. 16996-7010). At present, the main instruments for puncturing intrahepatic portal vein branches during TIPS surgery are RUPS-100 produced by Cook in the United States, and other similar instruments have basically disappeared. The RUPS-100 puncture assembly consists of an outer sheath, an expander, a plastic guide tube, a metal guide tube, a plastic sleeve and a puncture needle (Chu Jianguo, Development status and standardization of transjugular intrahepatic portal shunt technique in China, Chinese Electronic Journal of Interventional Radiology, 2013, 1 (2)).

However, the puncture assembly is designed according to the body type and vascular network characteristics of the European and American race, and it is not fully suitable for the body type of Asians and Chinese patients with liver atrophy mainly from hepatitis B lesions to cirrhosis. In practice, the adoption of this puncture assembly for portal vein branch puncture has a low hit rate, which not only causes more pain for the patient, but also requires the doctor and the patient to suffer a larger dose of X-ray irradiation. More seriously, this may also cause the surgery implementer to penetrate the liver capsule into the main portal vein of the liver by mistake, resulting in serious complications such as massive abdominal hemorrhage or the like.

Therefore, generally before performing intrahepatic portal vein branch puncture, the surgery implementer must carefully study the results of portal venography, and manually adjusts RUPS-100 by hands in vitro (in most cases, it is necessary to increase the bending angle of the puncture needle) based on position and shape of the portal vein and the relationship between the hepatic vein and the portal vein branch all of which are displayed by the above portal venography, and the anatomical relationship between hepatic and portal veins usually varies greatly from individual to individual. Whether the bending angle of the metal guide tube is appropriate and whether the inner diameter is curved to be flat can only depend on the experience of the surgery implementer.

Since the surgery is performed with the eye of the doctor, the position of the puncture needle and the position relationship between the puncture needle and various parts of the subject's body are judged during the surgery also depending on the experience of the surgery implementer.

In addition, because the subject's body position during the surgery and breathing movements may cause liver displacement and thus results in position deviation, even an experienced implementer usually needs to perform many times of puncture (about 5 to 8 times, even 10 to 15 times) to achieve success. The more the times of puncture is, the more opportunities the occurrence of complications is, and this is also the cause of postoperative restenosis and acute thrombosis (Li Yanhao. Diagram of Practical Clinical Interventional Diagnosis and Treatment [M]. Beijing: Science Press, 2012.).

There is an urgent need for a TIPS portal vein puncture system that is suitable for a variety of body sizes of crowds and livers of various cirrhosis lesions with no monitoring blind areas, and reduces surgical complications.

Therefore, puncture surgery, especially one with a narrow and tortuous puncture path, having an angular requirement and passing through important tissues and organs, such as TIPS portal vein puncture, has a high degree of operation difficulty, poor accuracy, poor safety, results in complications easily, and has surgical monitoring blind zones, which has become an urgent problem to be solved.

SUMMARY

Accordingly, embodiments of the present disclosure provide a puncture system which is configured with interventional navigation technology and corresponding puncture instruments to solve one or more of the above problems of the existing puncture surgery that has a high degree of operation difficulty, poor accuracy and poor safety, susceptibility to complications, and has surgical monitoring blind zones, so as to operate a puncture surgery that is easier to operate, more accurate and effective, safer, and with fewer complications.

According to one aspect of the disclosure, the disclosure provides a puncture system including: an interventional navigation system and a puncture instrument; the interventional navigation system includes an electromagnetic positioning module, a navigation processing module and a navigation output module, and the electromagnetic positioning module is connected with an ultrasonic imaging device and the puncture instrument, configured to obtain position and direction of an ultrasonic image generated by the ultrasonic imaging device and position and direction of the puncture instrument; the navigation processing module is connected with the ultrasonic imaging device and the electromagnetic positioning module, configured to generate a puncture path based on the position and direction of the puncture instrument, and orthographically project the puncture instrument and the puncture path onto the ultrasonic image to generate a navigation image that fuses a projection of the puncture instrument and the puncture path based on the position and direction of the ultrasonic image, the position and direction of the puncture instrument, and the puncture path; and the navigation output module is connected with the navigation processing module, configured to output the navigation image base on the set display mode.

Further, the puncture instrument includes a puncture needle which includes a sensor mounting portion, and the sensor mounting portion is capable of mounting a sensor of the electromagnetic positioning module.

Further, the sensor mounting portion is an internal cavity of the puncture needle or a concave portion of body surface of the puncture needle.

Further, the puncture needle is tubular, one end of a tubular cavity of the puncture needle is opened at a proximal end of the puncture needle, the other end of the tubular cavity is closed at a distal end of the puncture needle, and the sensor mounting portion is formed by the tubular cavity.

Further, the puncture needle includes a needle head and a needle rod, and the needle head and the needle rod are formed integrally.

Further, the puncture needle includes a needle head and a needle rod, and the needle head and the needle rod are connected by welding or threading.

Further, the proximal end of the needle head includes a connection portion, the needle rod is tubular, and when the needle head is connected with the needle rod, the connection portion is inserted into the tubular cavity of the needle rod.

Further, an outer diameter of a distal portion of the needle rod is smaller than an outer diameter of a proximal portion of the needle rod.

Further, the needle rod includes an inner needle rod and an outer needle rod, and the outer needle rod sleeves outside the inner needle rod, and the outer needle rod is connected with the inner needle rod by welding.

Further, the inner needle rod and the outer needle rod are sealed by welding or bonding.

Further, at the distal portion of the needle rod, the inner needle rod extends beyond the outer needle rod.

Further, the puncture needle includes an auxiliary portion, the auxiliary portion sleeves outside the needle rod, and a friction coefficient of the auxiliary portion is smaller than that of the needle rod.

Further, the auxiliary portion is a spring or a sleeve.

Further, the spring is connected with the needle rod by welding.

Further, a material of the sleeve is polytetrafluoroethylene, and the sleeve is connected with the needle rod by heat shrinkage.

Further, the outer diameter of a distal portion of the needle rod is smaller than an outer diameter of a proximal portion of the needle rod, and the spring or the sleeve sleeves at the distal portion of the needle rod.

Further, the outer needle rod includes a distal outer needle rod and a proximal outer needle rod, the distal outer needle rod sleeves at a distal end of the inner needle rod, the proximal outer needle rod sleeves at a proximal end of the inner needle rod, and the spring or the sleeve sleeves outside the inner needle rod between the distal outer needle rod and the proximal outer needle rod.

Further, an outer diameter of a distal portion of the inner needle rod is smaller than an outer diameter of a proximal portion of the inner needle rod, and the outer needle rod and the spring sequentially sleeve at the distal portion of the inner needle rod from the distal end to the proximal end, or the outer needle rod and the sleeve sequentially sleeve at the distal portion of the inner needle rod from the distal end to the proximal end.

Further, at the distal portion of the needle rod, the inner needle rod extends beyond the outer needle rod, and the spring or the sleeve sleeves at the portion of the inner needle rod that extends beyond the outer needle rod.

Further, the sensor is a wireless sensor or a wired sensor.

Further, a material of the puncture needle includes but is not limited to one or more selected from stainless steel, and nickel-titanium alloy.

Further, a thickness specification of the puncture needle includes but are not limited to 16G, 17G, 18G, 19G, 20G, and 21G.

Further, a material of the spring includes but is not limited to one or more selected from stainless steel, nickel-titanium alloy, cobalt-based alloy, and titanium-based alloy.

Further, the puncture instrument includes an interventional catheter instrument, which includes: a guide tube; and a flexible sleeve which sleeves outside the guide tube; and the flexible sleeve and the guide tube are capable of moving relatively to each other so that a distal end of the flexible sleeve extends beyond a distal end of the guide tube, or the distal end of the guide tube extends beyond the distal end of the flexible sleeve.

Further, the distal end of the flexible sleeve is provided with a shrunk portion, an inner diameter of the shrunk portion is smaller than the outer diameter of the guide tube, and the shrunk portion is provided with a weakened portion which is easy to be damaged; when the interventional catheter instrument abuts against a puncture target, the weakened portion is capable of being destroyed by causing the guide tube to move to the distal end relative to the flexible sleeve, so that the guide tube extends beyond the distal end of the flexible sleeve.

Further, the weakened portion extends to a distal opening of the flexible sleeve.

Further, the weakened portion extends to the distal opening of the flexible sleeve in a longitudinal direction of the flexible sleeve in a straight or helical manner.

Further, the weakened portion is an intermittent indent line or indentation.

Further, the weakened portion is provided on an inner surface or an outer surface of the shrunk portion.

Further, the inner diameter of the shrunk portion is smaller than the outer diameter of the guide tube of 0.05 mm to 1 mm.

Further, a material of the flexible sleeve includes, but are not limited to, one or more selected from polytetrafluoroethylene, fluorinated ethylene propylene copolymer, thermoplastic polyurethane elastomer, nylon 12, block polyether amide elastomer, and high density poly-ethylene.

Further, a material of the guide tube includes but is not limited to one or more selected from stainless steel, and nickel-titanium alloy.

Further, a thickness specification of the guide tube includes but are not limited to 13G, 14G, 15G, and 16G, and a length of the guide tube is 42 cm to 57 cm.

Further, the inner diameter of the flexible sleeve is greater than the outer diameter of the guide tube of 0.1 mm to 2 mm.

Further, the interventional catheter instrument includes a connector through which a proximal end of the guide tube is connected with a proximal end of the flexible sleeve, and the guide tube and the flexible sleeve are able to move relative to each other through the connector.

Further, a connection method of the connector includes threaded connection, clasping connection or bonding connection.

Further, when the puncture instrument and the ultrasonic image are in a coplanar state and a non-coplanar state, the navigation image is displayed differently.

Further, the navigation image is displayed in a three-dimensional perspective.

Further, when the puncture instrument and the ultrasonic image are in a coplanar state and a non-coplanar state, the projection of the puncture instrument is displayed differently, and/or the projection of the puncture path is displayed differently.

Further, the projection of the puncture instrument and/or the projection of the puncture path are displayed by, but not limited to, one or combination of more selected from line frame display, surface display, solid line display, dashed line display, various color display, dynamic display, and static display.

Further, when the puncture instrument and the ultrasonic image are in a non-coplanar state, and an intersection point of the puncture path with the ultrasonic image is displayed differently from other points on the projection of the puncture path.

Further, the intersection point is displayed by, but not limited to, one or combination of more selected from crossed lines display, starlike display, circular display, various color display, and dynamic display.

Further, when the puncture instrument and the ultrasonic image are in a non-coplanar state, projections of two portions of the puncture path on two sides of the ultrasonic image are displayed respectively in different ways, and/or projections of two portions of the puncture instrument on two sides of the ultrasonic image are displayed respectively in different ways.

Further, the projections of the two portions of the puncture instrument and/or the projections of the two portions of the puncture path are displayed by, but not limited to, one or combination of more selected from line frame display, surface display, solid line display, dashed line display, various color display, dynamic display, and static display.

Further, the puncture path in a straight line shape is formed by extending in the direction of the puncture instrument.

Further, the electromagnetic positioning module includes a first sensor connected to a probe of the ultrasonic imaging device and a second sensor connected to the puncture instrument.

In summary, the puncture system according to the present disclosure utilizes intervention navigation technology and a corresponding puncture instrument to implement puncture surgery that is easier to operate, more accurate and effective, safer, and with fewer complications, and that has no blind zones during surgery monitoring, so as to solve the technical problems in the prior art.

BRIEF DESCRIPTION OF THE DRAWINGS

The features and advantages of the present disclosure will become more easily understood by the following specific embodiments provided with reference to the attached drawings, in the drawings.

DESCRIPTION OF THE EMBODIMENTS

The exemplary embodiments of the present disclosure are described below in detail with reference to the attached drawings. The description of the exemplary embodiments is for illustration purposes only and is in no way a limitation to the present disclosure and its application or usage.

In order to make the purpose, advantages and features of the disclosure clearer, the present disclosure is further illustrated in detail in combination with the attached drawings. It should be noted that the drawings are in a very simplified form and use imprecise proportions only to conveniently and clearly assist in stating the purpose of embodiments of the present disclosure.

As used in the present disclosure, the singular forms "a", "an", and "the" include plural objects, unless the content expressly states otherwise. As used in the present disclosure, the term "or" is generally used in a sense that includes "and/or" unless otherwise expressly stated in the content. The "distal end" and "distal side" mentioned in the present disclosure refer to the side far away from the operator; and accordingly, "proximal end" and "proximal side" refer to the side opposite to "distal end" and "distal side".

The present disclosure provides a puncture system which is configured with interventional navigation technology and corresponding puncture instruments to solve one or more of the problems of the existing puncture surgery that has a high degree of operation difficulty, poor accuracy and poor safety, susceptibility to complications, so as to implement a puncture surgery that is easier to operate, more accurate and effective, safer, and with fewer complications.

Figure 1:
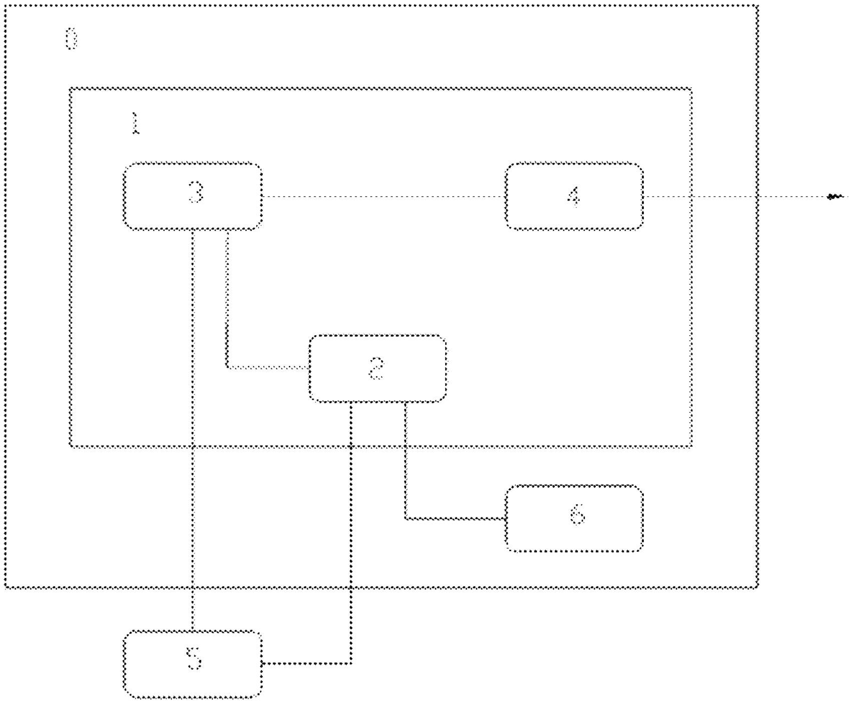
FIG. 1 is a schematic diagram of a puncture system according to an embodiment of the present disclosure.

FIG. 1 is a schematic diagram of a puncture system according to an embodiment of the present disclosure. As shown in FIG. 1, in an embodiment of the present disclosure, the puncture system 0 includes an interventional navigation system 1 and a puncture instrument 6, and the interventional navigation system 1 includes an electromagnetic positioning module 2, a navigation processing module 3 and a navigation output module 4.

In this embodiment, the electromagnetic positioning module 2 is connected with an ultrasonic imaging device 5 and the puncture instrument 6, configured to obtain position and direction of an ultrasonic image generated by the ultrasonic imaging device 5 and position and direction of the puncture instrument 6.

The interventional instrument is a device configured to perform interventional diagnosis and treatment, such as a vascular stent kit, a percutaneous biopsy kit, a radiofrequency ablation kit, a tumor embolization kit, etc. The interventional instrument may include but is not limited to one or more selected from a puncture instrument, a radiofrequency instrument, a microwave instrument, a particle instrument, an implantable instrument, a sheath instrument, a tube instrument, a biopsy instrument, etc. The interventional instrument may include one or more interventional tools, and the interventional tool may be a catheter, a guidewire, a puncture needle, a vascular sheath, a balloon, a biopsy needle, etc.

The interventional navigation system 1 can be used in conjunction with other interventional instruments as required.

The electromagnetic positioning module 2 of the embodiment of the present disclosure uses electromagnetic induction to measure the position and direction of an object based on the Biot-Savart rule, in which a magnetic field signal sender generates a signal field by sending a magnetic field signal, and a magnetic signal receiving sensor receives the magnetic field signal and transmits the magnetic field signal to a magnetic field signal controller to obtain space vector information (space coordinates and direction) of the object.

The precision of electromagnetic positioning technology can effectively solve the problem of inaccurate interventional navigation caused by the volume effect of the ultrasonic imaging device.

Figure 2:
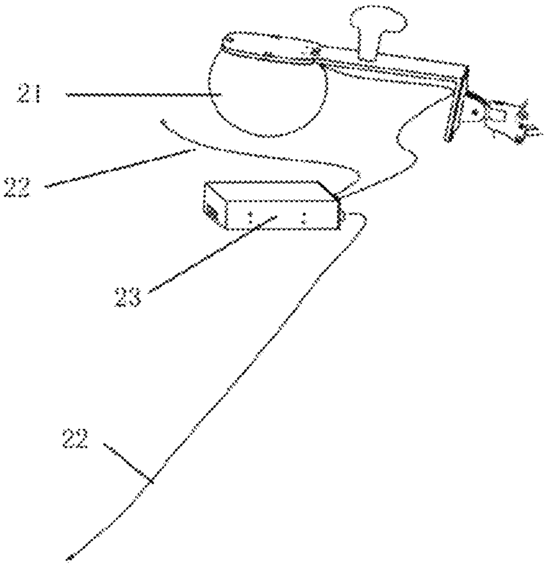
FIG. 2 is a schematic diagram of an electromagnetic positioning module according to an embodiment of the present disclosure.

FIG. 2 is a schematic diagram of an electromagnetic positioning module according to an embodiment of the present disclosure. As shown in FIG. 2, the electromagnetic positioning module 2 of the embodiment of the present disclosure includes a sender 21, a sensor 22 and a magnetic field signal processor 23. At present, the more widely used products are POLARIS system of Canada NDI company, VISLAN system of British RMR company, Stealthstation system of American Medtronic company, etc.; in which the POLARIS system has a measurement accuracy of 0.35 mm RMS, which is considered as the international standard for navigation and positioning systems and is capable of tracking nine passive and three active targets simultaneously.

The sender 21 includes an electromagnetic sender coil to emit electromagnetic waves to generate an electromagnetic field. The effective positioning range of the electromagnetic field in the embodiment of the present disclosure may be 300 mm×300 mm×300 mm, and 400 mm×400 mm×400 mm, etc.

The sensor 22 receives the electromagnetic signal emitted by the sender 21 through the electromagnetic receiving coil, converts the electromagnetic signal into an electrical signal, and tracks and positions the position and direction of sensor 22 located in the electromagnetic field through the magnetic field signal processor 23.

According to clinical requirements, the positioning accuracy of interventional navigation is usually up to 5 mm and the positioning speed is up to 30 ms. In the embodiment of the present disclosure, the minimum accuracy of electromagnetic positioning can be 1.5 mm, and the maximum positioning speed can be 12.5 ms. Further, in the implementation of the present disclosure, the electromagnetic positioning module 2 is capable of adjusting the positioning accuracy and positioning speed according to the needs.

Figure 3:
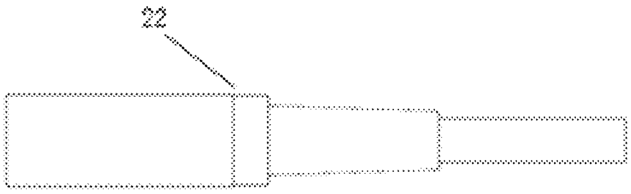
FIG. 3 is a schematic diagram of a sensor according to an embodiment of the present disclosure.
Figure 4:
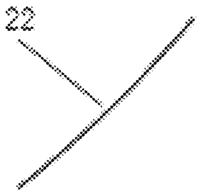
FIG. 4 is a schematic diagram of a sensor according to an embodiment of the present disclosure.

FIGS. 3 and 4 are schematic diagrams of a sensor according to an embodiment of the present disclosure. According to the application needs, the sensor 22 may be designed into various structures and sizes, and the size of the sensor 22 in the embodiment of the present disclosure can be the minimum outer diameter of 0.56 mm. As shown in FIG. 3, the sensor 22 may be designed as a column shape with a large diameter, and is suitable for being mounted on the ultrasonic probe. As shown in FIG. 4, the sensor 22 may also be designed as a line shape with a small diameter, and is suitable for being mounted on the interventional instrument such as the puncture instrument.

The sensor 22 can be wired or wireless, thus the connection between the electromagnetic positioning module 2 and the ultrasonic imaging device 5 and connection between the electromagnetic positioning module 2 and the puncture instrument 6, may be wired or wireless, such as Bluetooth, WIFI, Zigbee, etc.

Figure 5:
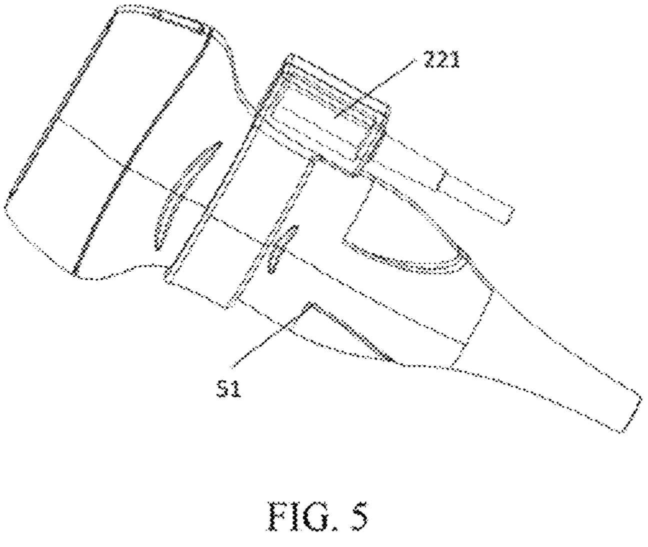
FIG. 5 is a schematic diagram of an ultrasonic probe provided with a sensor according to an embodiment of the present disclosure.

FIG. 5 is a schematic diagram of an ultrasonic probe provided with a sensor according to an embodiment of the present disclosure. As shown in FIG. 5, the sensor 221 is detachably mounted on the ultrasonic probe 51 so that the electromagnetic positioning module 2 is capable of tracking and positioning the position and direction of the ultrasonic probe 51. According to the relationship between the ultrasonic probe 51 and the ultrasonic image generated by the ultrasonic imaging device 5, the electromagnetic positioning module 2 is capable of tracking and positioning the position and direction of the ultrasonic image generated by the ultrasonic imaging device 5.

Figure 6:
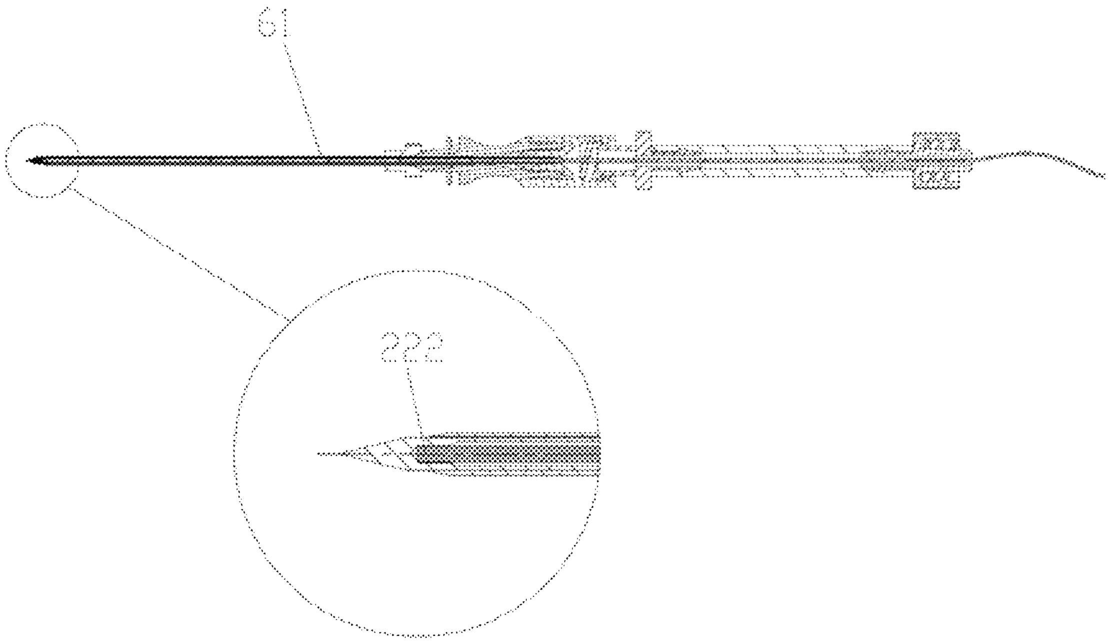
FIG. 6 is a schematic diagram of a puncture needle provided with a sensor according to an embodiment of the present disclosure.

In the embodiment of the present disclosure, the puncture instrument 6 may include a puncture needle 61. FIG. 6 is a schematic diagram of a puncture needle provided with a sensor according to an embodiment of the present disclosure. As shown in FIG. 6, the sensor 222 is detachably provided within a needle cavity of the puncture needle 61.

In order to adapt to the puncture instruments 6 of different lengths, auxiliary connectors with different lengths may be provided to connect the sensor to the puncture instrument 6.

The electromagnetic positioning module 2 is capable of tracking and positioning the position and direction of the puncture needle 61 by the sensor 222 provided on the puncture instrument 6.

The magnetic field signal processor 23 collects and tracks an electrical signal of positioning data in real time, calculates the real-time position and real-time direction of the sensor, and transmits result information of the calculation to the navigation processing module 3 in real time.

As shown in FIG. 1, the navigation processing module 3 is connected to the ultrasonic imaging device 5, configured to obtain the ultrasonic image. As shown in FIG. 1, the navigation processing module 3 is connected to the electromagnetic positioning module 2, configured to obtain the ultrasonic image and the position and direction of the puncture instrument 6.

In the embodiment of the present disclosure, the navigation processing module 3 generates a puncture path 64 based on the position and direction of the puncture instrument 6, and orthographically projects the puncture instrument 6 and the puncture path 64 onto the ultrasonic image to generate a navigation image that fuses a projection of the puncture instrument 6 and the puncture path 64 based on the position and direction of the ultrasonic image, the position and direction of the puncture instrument 6, and the puncture path 64.

In the embodiment of the present disclosure, the navigation processing module 3 can be connected to the ultrasonic imaging device 5 through a video image collection device to obtain ultrasonic image data. In an embodiment, the connection is realized through USB3.0 connection, which may also be PCI (Peripheral Component Interconnect) or PCIE (Peripheral Component Interconnect Express).

In the embodiment of the present disclosure, exemplarily, the video collection device may be interfaced with an all-digital color Doppler ultrasonic diagnostic system DVI (Digital Visual Interface) or HDMI (High Definition Multimedia Interface) through a high-definition video cable with shielding or in a wireless manner to collect real-time ultrasonic video, and to convert the ultrasonic video into a digital signal which is transmitted to the navigation processing module 3.

The video collection device of the embodiment of the present disclosure has a standard video interface, such as HDMI or DVI, which can be connected with the standard video interface of the existing ultrasonic imaging device through a standard video signal line. Therefore, the interventional navigation system of the embodiment of the present disclosure can be compatible with various ultrasonic imaging devices, thus on the one hand, the existing ultrasonic imaging device can be fully utilized, and on the other hand, the volume and weight of the interventional navigation system can be smaller, more flexible, and convenient to use.

In the embodiment of the present disclosure, the ultrasonic imaging device 5 may be a black and white ultrasonic system, an all-digital color Doppler ultrasonic diagnostic system, etc.

In the embodiment of the present disclosure, the navigation processing module 3 and the electromagnetic positioning module 2 may be connected through a USB (Universal Serial Bus) interface and adopted a USB2.0 protocol, to obtain the ultrasonic image and the position and direction data of the puncture instrument 6 from the electromagnetic positioning module 2.

In the embodiment of the present disclosure, the navigation processing module 3 is capable of generating the puncture path 64 based on the shape of the puncture instrument 6, position and direction of the puncture instrument 6 and the needs of interventional diagnosis and treatment, and the puncture path 64 is usually a straight line extending in the direction of the puncture instrument 6.

Figure 7:
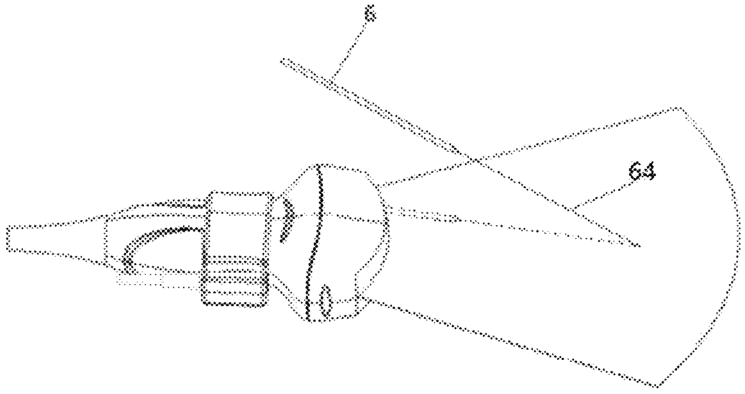
FIG. 7 is a schematic diagram of a navigation image generated by fusion according to an embodiment of the present disclosure.

FIG. 7 is a schematic diagram of a navigation image generated by fusion according to an embodiment of the present disclosure. As shown in FIG. 7, in the embodiment of the present disclosure, based on the position and direction of the ultrasonic image, the position and direction of the puncture instrument 6, and the position and direction of the puncture path 64, the navigation processing module 3 is capable of orthographically projecting the puncture instrument 6 and the puncture path 64 onto the ultrasonic image, to be fused with the ultrasonic image to generate a navigation image that fuses the information of the ultrasonic image, the puncture instrument and the puncture path.

As shown in FIG. 1, in the embodiment of the present disclosure, the navigation output module 4 is connected to the navigation processing module 3, configured to obtain navigation image data from the navigation processing module and output the navigation image data to a display device in a clearer and more intuitive display manner based on the set display mode, so as to provide interventional navigation for the medical staff performing intervention.

The navigation image may be displayed in a two-dimensional or three-dimensional perspective display mode.

In the embodiment of the disclosure, when the puncture instrument 6 and the ultrasonic image are in a coplanar state and a non-coplanar state, the navigation image can be displayed differently to provide interventional navigation more clearly and more intuitively.

Figure 8:
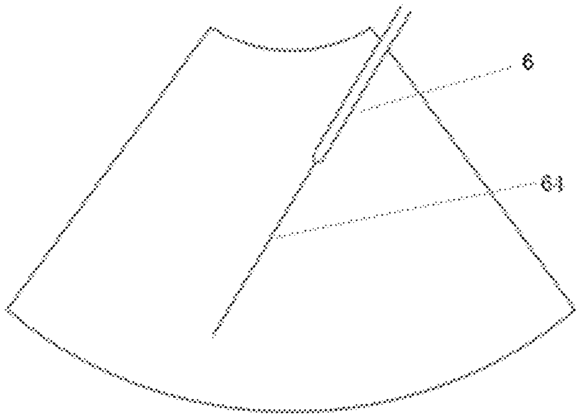
FIG. 8 is a schematic diagram of navigation image display when the puncture instrument and the ultrasonic image are in a coplanar state according to an embodiment of the present disclosure.

For example, FIG. 8 is a schematic diagram of navigation image display when the puncture instrument and the ultrasonic image are in a coplanar state according to an embodiment of the present disclosure. As shown in FIG. 8, in the embodiment of the present disclosure, when the puncture instrument 6 and the ultrasonic image are in a coplanar state, the projection of the puncture instrument 6 and the projection of the puncture path 64 may be displayed in the form of solid lines.

Figure 9:
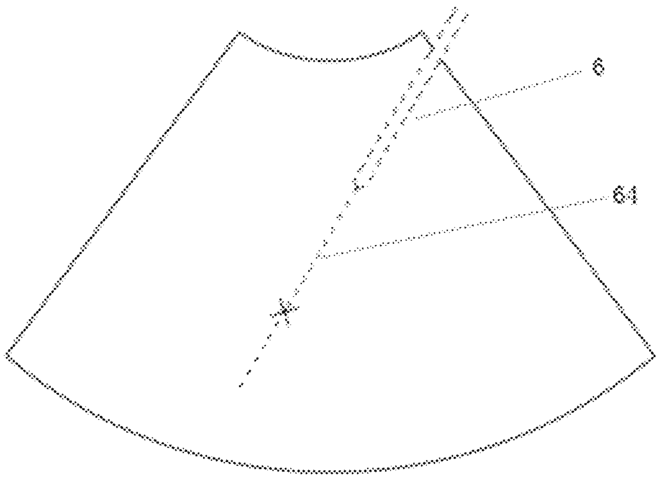
FIG. 9 is a schematic diagram of navigation image display when the puncture instrument and the ultrasonic image are in a non-coplanar state according to an embodiment of the present disclosure.

FIG. 9 is a schematic diagram of navigation image display when the puncture instrument and the ultrasonic image are in a non-coplanar state according to an embodiment of the present disclosure. As shown in FIG. 9, in the embodiment of the present disclosure, when the puncture instrument 6 and the ultrasonic image are in a non-coplanar state, the projection of the puncture instrument 6 and the projection of the puncture path 64 may be displayed in the form of dashed lines.

In the embodiment of the present disclosure, the projection of the puncture instrument 6 and/or the projection of the puncture path 64 may be displayed by, but not limited to, one or combination of more selected from line frame display, surface display, solid line display, dashed line display, various color display, dynamic display, and static display and the like.

In the embodiment of the present disclosure, when the puncture instrument 6 and the ultrasonic image are in a non-coplanar state, an intersection point of the puncture path 64 or the puncture instrument 6 with the ultrasonic image may be displayed differently from other points on the projection of the puncture path 64. As shown in FIG. 9, the intersection point of the puncture path 64 with the ultrasonic image is displayed in the form of crossed lines.

In the embodiment of the disclosure, the intersection point of the puncture path 64 with the ultrasonic image is displayed by, but not limited to, one or combination of more selected from crossed lines display, starlike display, various color display, dynamic display and the like.

In the embodiment of the present disclosure, when the puncture instrument 6 and the ultrasonic image are in a non-coplanar state, projections of two portions of the puncture path 64 on two sides of the ultrasonic image may be displayed respectively in different ways, and/or projections of two portions of the puncture instrument 6 on two sides of the ultrasonic image may be displayed respectively in different ways.

Figure 10:
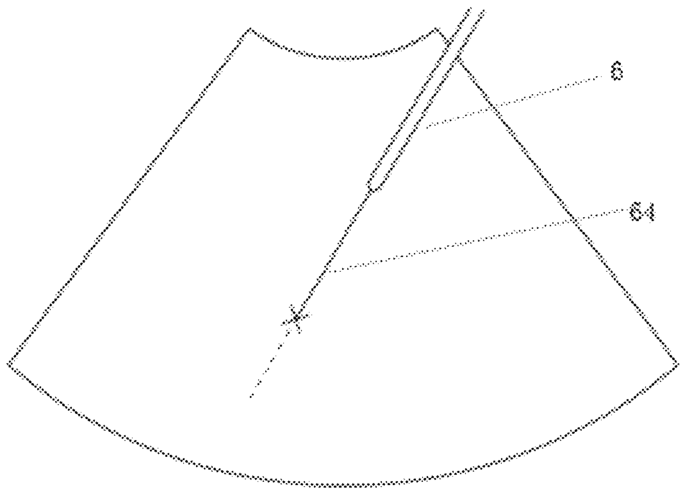
FIG. 10 is a schematic diagram of navigation image display when the puncture instrument and the ultrasonic image are in a non-coplanar state according to another embodiment of the present disclosure.

FIG. 10 is a schematic diagram of navigation image display when the puncture instrument and the ultrasonic image are in a non-coplanar state according to another embodiment of the present disclosure. As shown in FIG. 10, in the embodiment of the present disclosure, the projections of two portions of the puncture path 64 on two sides of the ultrasonic image may be displayed in the form of solid lines and dashed lines respectively.

In the embodiment of the disclosure, the projections of two portions of the puncture instrument 6 and/or the projections of two portions of the puncture path 64 may be displayed by, but not limited to, one or combination of more selected from line frame display, surface display, solid line display, dashed line display, various color display, dynamic display, and static display and the like.

In the embodiment of the present disclosure, when the puncture instrument 6 and the ultrasonic image are in a non-coplanar state, the position and direction of the puncture instrument 6 may be adjusted by navigating through the intersection point of the puncture path 64 with the ultrasonic image. When the intersection point coincides with a target point, the puncture path 64 intersects with the target point, so that the interventional navigation can be realized when the puncture instrument 6 and the ultrasonic image are in non-coplanar state.

In the embodiment of the present disclosure, according to the location layout of the sensor 222 in the puncture needle 61 and the structure of the puncture needle 61, the outline of the puncture needle 61 can be drawn and displayed, especially the real-time position and real-time direction of the working part of the puncture needle 61.

In the embodiment of the present disclosure, real-time guide and positioning can be realized to feed back the position and direction of the working part of the puncture needle and the puncture path, which is not restricted by the angle, has high safety, and is convenient and reliable to use.

In the embodiment of the present disclosure, the navigation processing module 3 and the navigation output module 4 may be realized by a computer system.

In the embodiment of the present disclosure, the interventional ultrasonic navigation system may also include a carrier, the carrier may include an operation table, an electromagnetic positioning module mounting member, a display mounting member, a power supply control module, a moving device, etc.

In the embodiment of the present disclosure, the operation table may be configured to temporarily place medical consumables or tools, as well as to mount, bear and lift of a display device and the electromagnetic positioning module, and may have the lifting and lowering function.

In the embodiment of the present disclosure, the electromagnetic positioning module mounting member may be configured to mount and bear the electromagnetic positioning module 2, and may be a hovering support arm or an independent bracket.

In the embodiment of the present disclosure, the display mounting member may be configured to mount and bear the display device, and may be a hovering support arm or an independent bracket.

In the embodiment of the present disclosure, the power supply control module may be a power supply control module conforming to the safety regulations of Chinese National Standards GB9706.1-2007, including a battery, the battery specification is not less than 14.8V/15.6 Ah.

In the embodiment of the present disclosure, the moving device may be a castor with a locking function.

In order to solve one or more of the above problems of the existing puncture surgery that has a high degree of operation difficulty, poor accuracy and poor safety, so as to implement a puncture surgery that is easier to operate, more accurate and effective, safer. The puncture instrument of the embodiment of the present disclosure may be applied to interventional navigation technology to implement a puncture surgery that is easier to operate, more accurate and effective, safer under interventional navigation.

Figure 11:
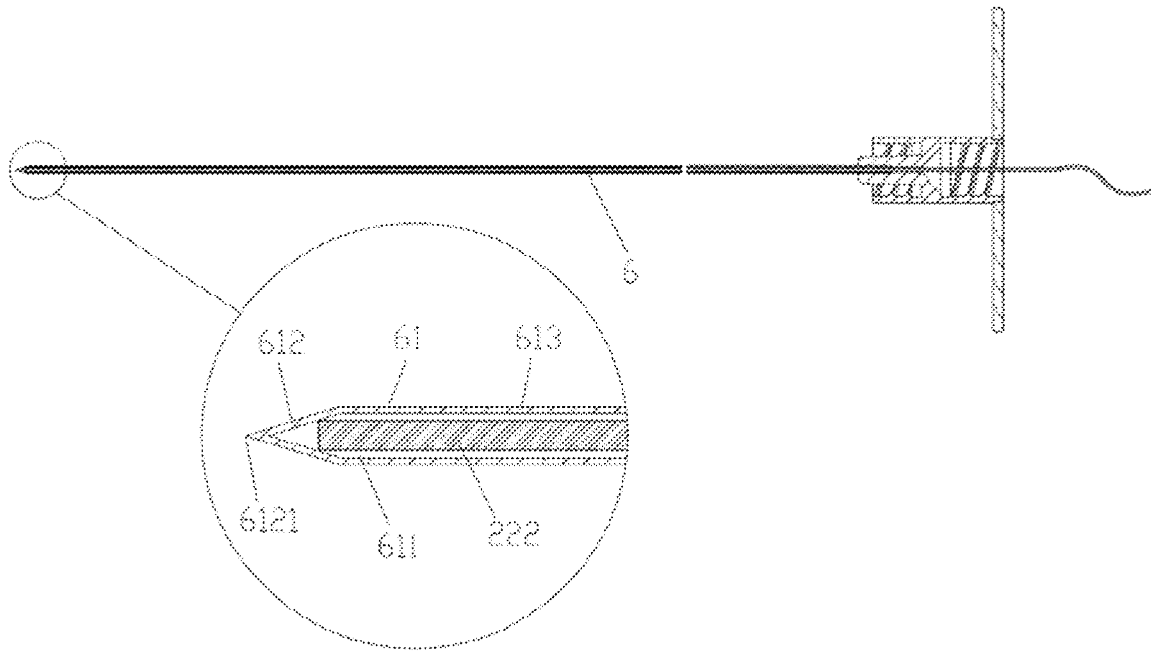
FIG. 11 is a schematic diagram of a puncture instrument according to an embodiment of the present disclosure.

FIG. 11 is a schematic diagram of a puncture instrument according to an embodiment of the present disclosure. As shown in FIG. 11, in the embodiment of the present disclosure, the puncture instrument 6 may include a puncture needle 61, the puncture needle 61 is capable of being provided with a sensor mounting portion 611, and the sensor mounting portion 611 may be configured to mount a sensor 222.

In the embodiment of the present disclosure, a material of the puncture needle 61 may include, but is not limited to, one or more selected from stainless steel, and nickel-titanium alloy.

According to the requirements of clinical application, a thickness specification of the puncture needle 61 can include, but is not limited to: 16G, 17G, 18G, 19G, 20G, 21G, etc. (G is the abbreviation of GAUGE, a length metering unit of diameter originating in North America).

According to the requirements of clinical application, the puncture needle 61 may be designed in various lengths, for example, for transjugular intrahepatic portosystemic shunt, the length specification may be 50 cm to 65 cm.

Figure 13:
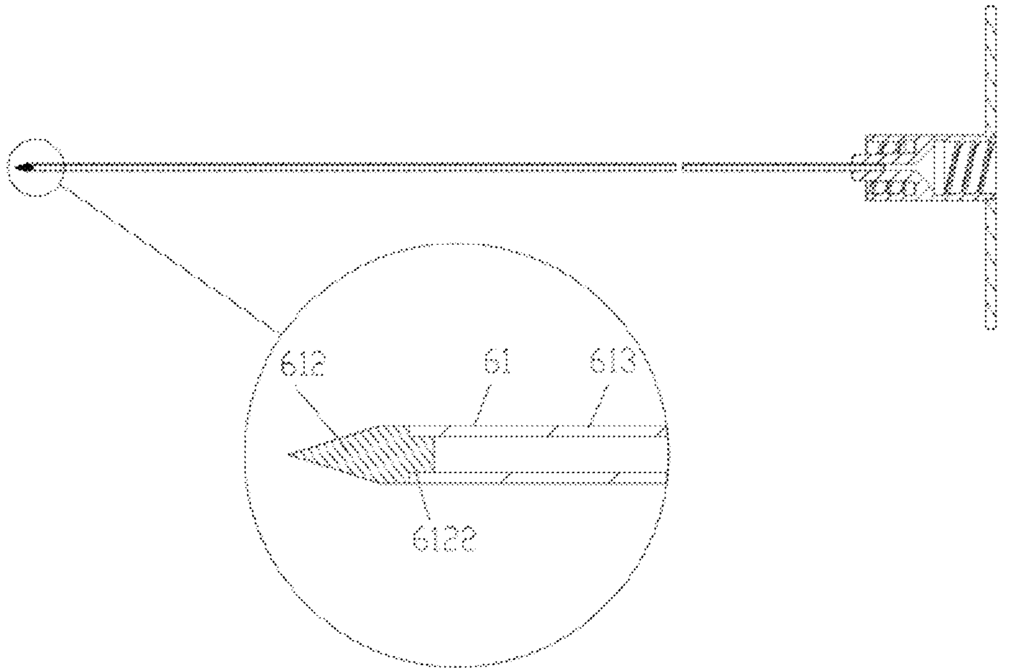
FIG. 13 is a schematic diagram of a puncture needle according to an embodiment of the present disclosure.

As shown in FIG. 11, the puncture needle 61 may include a needle head 612 and a needle rod 613. In the embodiment of the disclosure, the needle head 612 and the needle rod 613 may be formed integrally, as shown in FIG. 11. The needle head 612 and the needle rod 613 may also be assembly connected separately. For example, the needle head 612 and the needle rod 613 are connected by welding, threading, etc., as shown in FIG. 13.

In the embodiment of the present disclosure, a needle tip 6121 of the needle head 612 may be of a triangular pyramid, a rectangular pyramid or conical. The height of the taper of the needle tip 6121 may be 1 mm to 4 mm.

Since the puncture surgery navigation usually requires positioning the distal end of the puncture needle, in the embodiment of the present disclosure, the sensor mounting portion 611 may be provided on the distal end of the puncture needle 61.

In the embodiment of the present disclosure, the sensor mounting portion 611 may be an internal cavity of the puncture needle 61, as shown in FIG. 11. If the sensor is wired, the cavity may be provided with an opening for the pass-through the wire. For example, the cavity is opened at the proximal end of the puncture needle 61. If the sensor is wireless, the cavity may be closed after the sensor is installed.

In the embodiment of the present disclosure, the distance between the cavity of the puncture needle 61 and the needle tip of the puncture needle 61 may be 0.10 mm to 30 mm.

As shown in FIG. 11, the puncture needle 61 may be tubular, one end of a tubular cavity of the puncture needle 61 is opened at a proximal end of the puncture needle 61, the other end of the tubular cavity is closed at a distal end of the puncture needle, and the sensor mounting portion 611 is formed by the tubular cavity.

Figure 12:
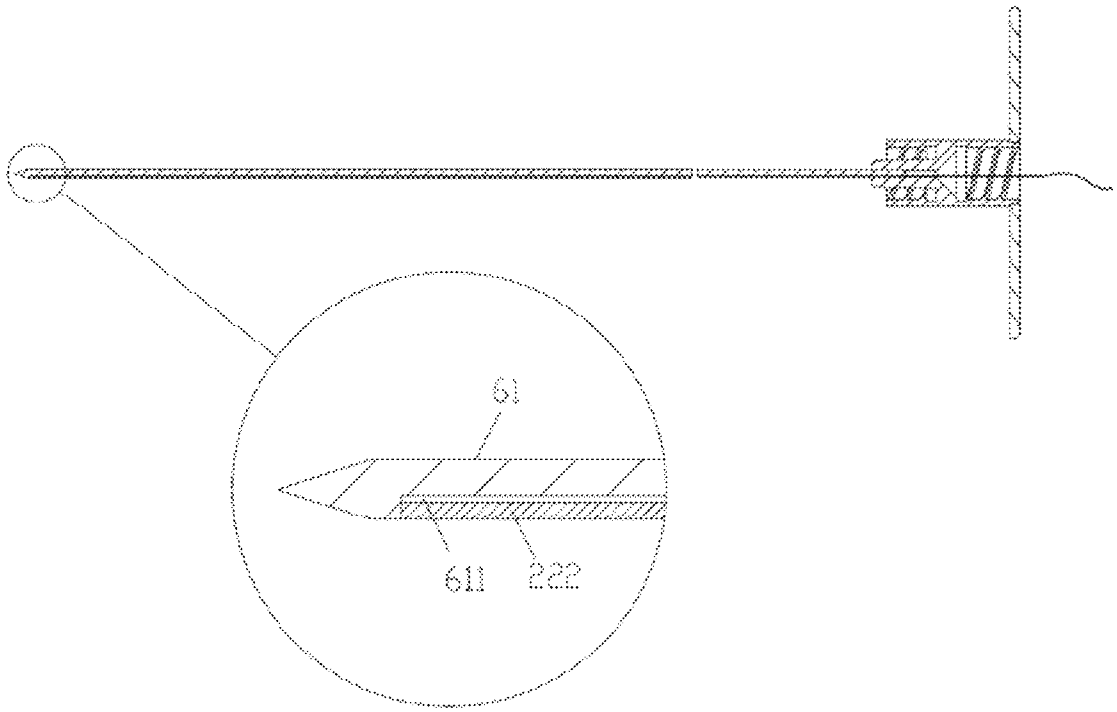
FIG. 12 is a schematic diagram of a puncture instrument according to an embodiment of the present disclosure.

FIG. 12 is a schematic diagram of a puncture instrument according to an embodiment of the present disclosure. As shown in FIG. 12, in the embodiment of the disclosure, the sensor mounting portion 611 may be a concave portion of body surface of the puncture needle 61.

FIG. 13 is a schematic diagram of a puncture needle according to an embodiment of the present disclosure. As shown in FIG. 13, the proximal end of the needle head 612 may include a connection portion 6122, and an outer diameter of the connection portion 6122 is smaller than an inner diameter of the tubular cavity of the needle rod 613. When the needle head 612 is connected to the needle rod 613, the connection portion 6122 is capable of being inserted into the tubular cavity of the needle rod 613.

In order to adapt to a tortuous and narrow puncture path and increase the flexibility and guidance of the puncture needle 61, in the embodiment of the present disclosure, the needle rod 613 may be set as a variable-diameter shape, and the outer diameter of the distal portion of the needle rod 613 is smaller than the outer diameter of the proximal portion of the needle rod 613. A transition between the two outer diameter portions may be gradual or stepped.

Figure 14:
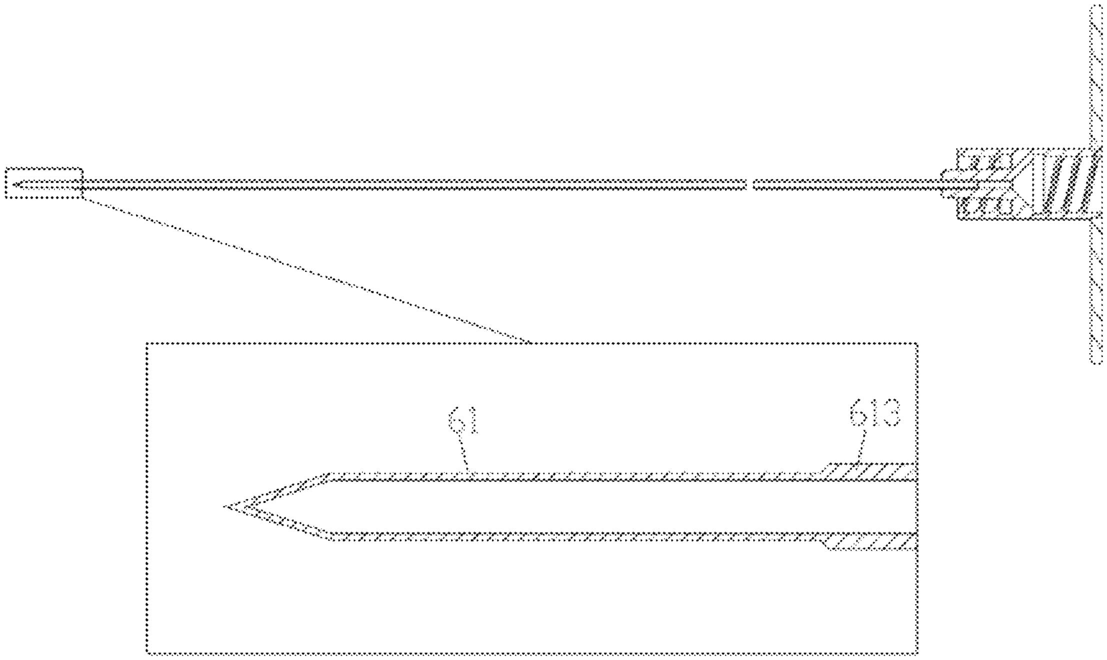
FIG. 14 is a schematic diagram of a puncture needle according to an embodiment of the present disclosure.

FIG. 14 is a schematic diagram of a puncture needle according to an embodiment of the present disclosure. As shown in FIG. 14, the outer diameter of the distal portion of the needle rod 613 is smaller than the outer diameter of the proximal portion of the needle rod 613, and a transition between the two outer diameter portions may be stepped. The flexibility and guidance of the needle rod 613 may be effectively increased by above reduced variable-diameter shape.

In order to adapt to a tortuous puncture path and increase the flexibility and guidance of the puncture needle 61, in the embodiment of the disclosure, the needle rod may also be configured to include an inner needle rod and an outer needle rod.

Figure 15:
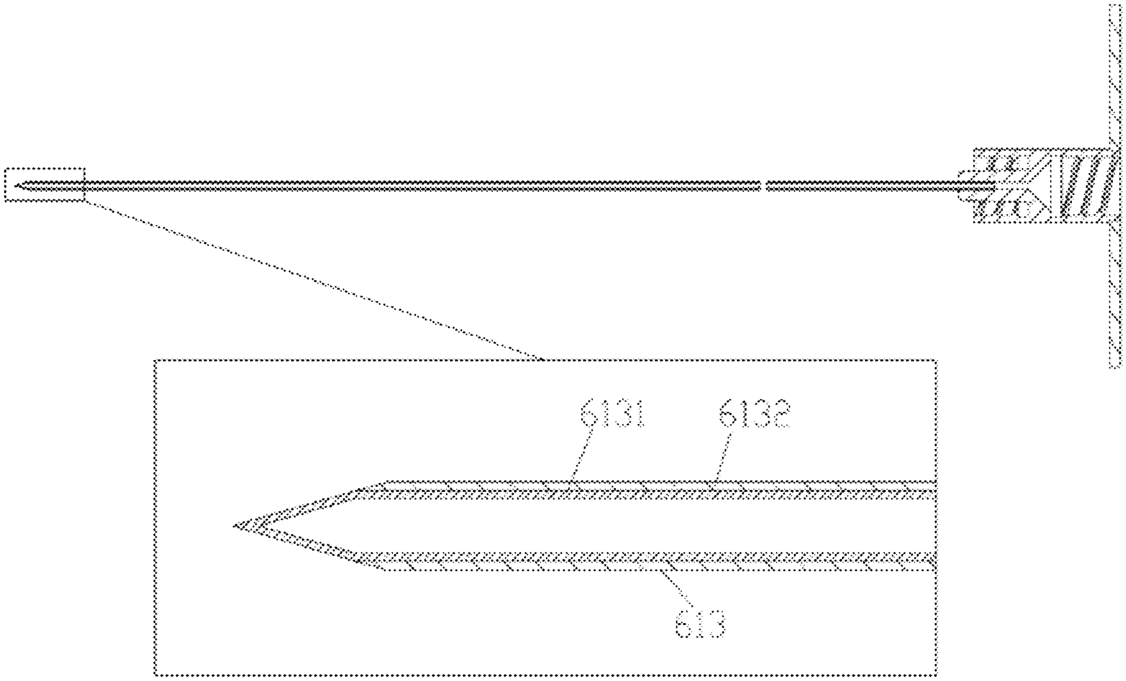
FIG. 15 is a schematic diagram of a puncture needle according to an embodiment of the present disclosure.

FIG. 15 is a schematic diagram of a puncture needle according to an embodiment of the present disclosure. As shown in FIG. 15, the needle rod 613 may include an inner needle rod 6131 and an outer needle rod 6132, and the outer needle rod 6132 sleeves outside the inner needle rod 6131. The outer needle rod 6132 and the inner needle rod 6131 may be connected by welding, threading, etc. In addition, in order to prevent body fluids from entering between the inner needle rod 6131 and the outer needle rod 6132, sealing treatment is required between the inner needle rod 6131 and the outer needle rod 6132, and the sealing treatment may be achieved by welding or bonding.

Figure 16:
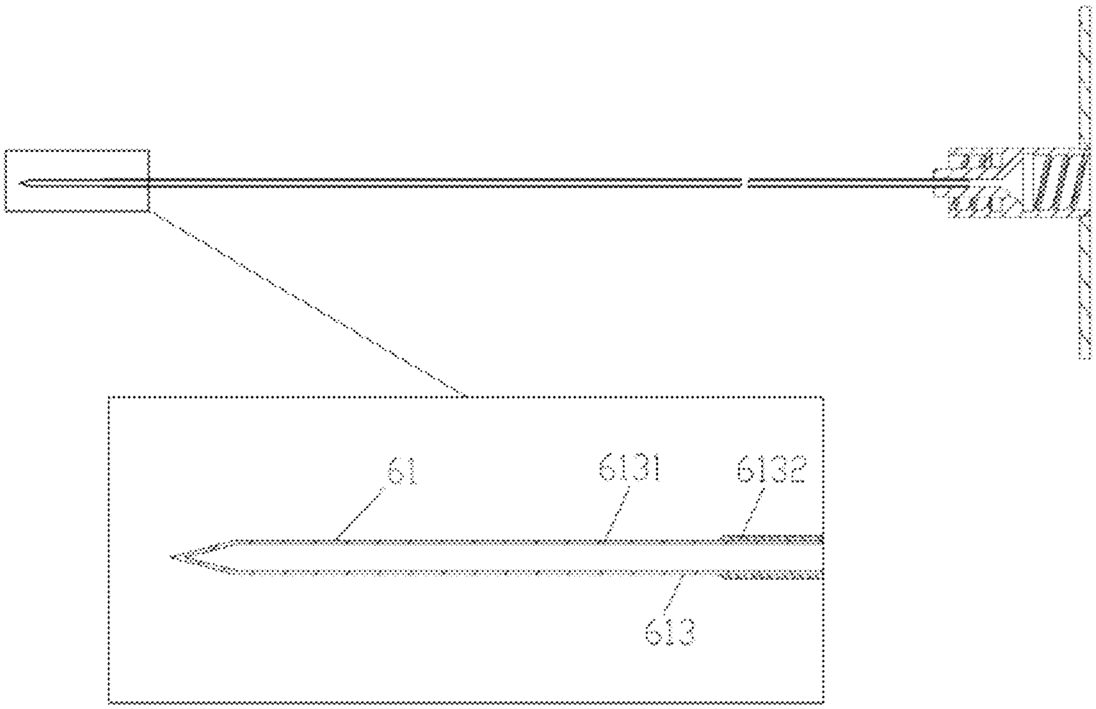
FIG. 16 is a schematic diagram of a puncture needle according to an embodiment of the present disclosure.

In the embodiment of the present disclosure, the design of the reduced variable-diameter needle rod may be combined with the design of the inner needle rod and the outer needle rod. FIG. 16 is a schematic diagram of a puncture needle according to an embodiment of the present disclosure. As shown in FIG. 16, at the distal portion of the needle rod 613, the inner needle rod 6131 extends beyond the outer needle rod 6132, resulting in a reduced variable-diameter needle rod design.

In order to adapt to a tortuous and narrow puncture path, effectively reduce the friction resistance of the puncture needle 61 and improve the operation stability of the puncture needle 61, in the embodiment of the disclosure, the puncture needle may also be configured to include an auxiliary portion, and the auxiliary portion may be a spring or a sleeve.

The spring can effectively reduce the contact area between the outer surface of the puncture needle 61 and the surrounding material, thereby reducing its friction resistance. In addition, due to its elastic tensile force and the effect of increasing the radial size of the puncture needle 61, the spring can improve the operation stability of the puncture needle 61.

The spring can sleeve on the needle rod and can be connected to the needle rod by welding. For example, both ends of the spring may be welded separately to the needle rod.

The sleeve can be made of a material with a low friction coefficient to reduce friction resistance, such as polytetrafluoroethylene (PTFE) material. The friction coefficient of polytetrafluoroethylene (PTFE) is very low, and the friction coefficient of polytetrafluoroethylene on steel is often quoted as 0.04. In addition, due to its elastic tensile force and the effect of increasing the radial size of the puncture needle 61, the sleeve can improve the operation stability of the puncture needle 61.

In the embodiment of the disclosure, the sleeve can sleeve on the needle rod by means of heat shrinkage.

Figure 17:
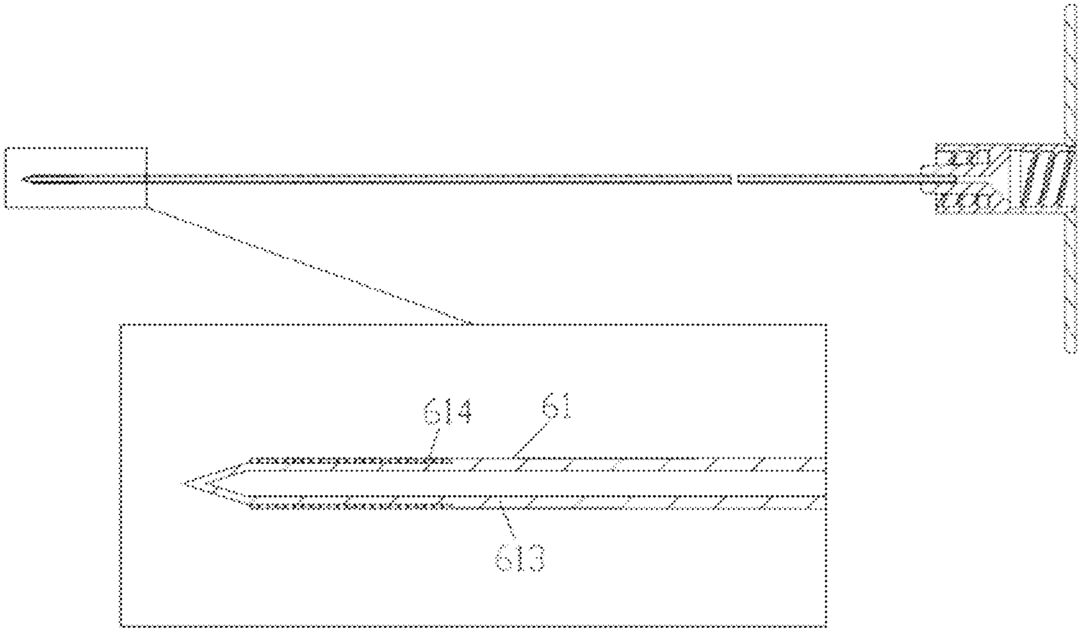
FIG. 17 is a schematic diagram of a puncture needle provided with a spring according to an embodiment of the present disclosure.

FIG. 17 is a schematic diagram of a puncture needle provided with a spring according to an embodiment of the present disclosure. As shown in FIG. 17, the needle rod 613 may be a variable-diameter shape, and the outer diameter of the distal portion of the needle rod 613 is smaller than the outer diameter of the proximal portion of the needle rod 613, and the spring 614 sleeves at the distal portion with a smaller outer diameter of the needle rod 613. The spring 614 may be connected with the needle rod 613 by welding.

In the embodiment of the disclosure, a material of the spring 614 may include, but is not limited to one or more selected from stainless steel, nickel-titanium alloy, cobalt-based alloy, and titanium-based alloy.

In the embodiment of the disclosure, a dimension of the spring 614 may be: diameter of a spring wire of 0.08 mm to 0.3 mm, mean diameter of coil of 0.5 mm to 2.0 mm, free length of the spring of 30 mm to 200 mm.

Figure 18:
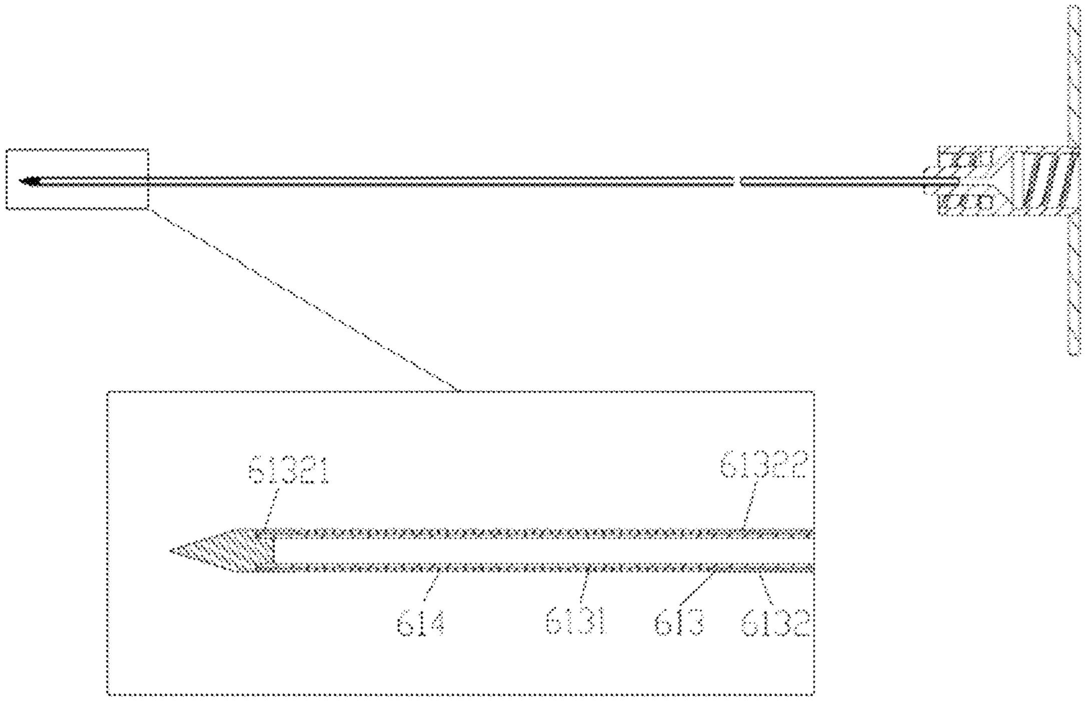
FIG. 18 is a schematic diagram of a puncture needle provided with a spring according to an embodiment of the present disclosure.

FIG. 18 is a schematic diagram of a puncture needle provided with a spring according to an embodiment of the present disclosure. As shown in FIG. 18, in the embodiment of the present disclosure, the outer needle rod 6132 may include a distal outer needle rod 61321 and a proximal outer needle rod 61322. The distal outer needle rod 61321 sleeves on a distal end of the inner needle rod 6131, the proximal outer needle rod 61322 sleeves on a proximal end of the inner needle rod 6131, and the spring 614 may be provided between the distal outer needle rod 61321 and the proximal outer needle rod 61322, and sleeves on the inner needle rod 6131.

Figure 19:
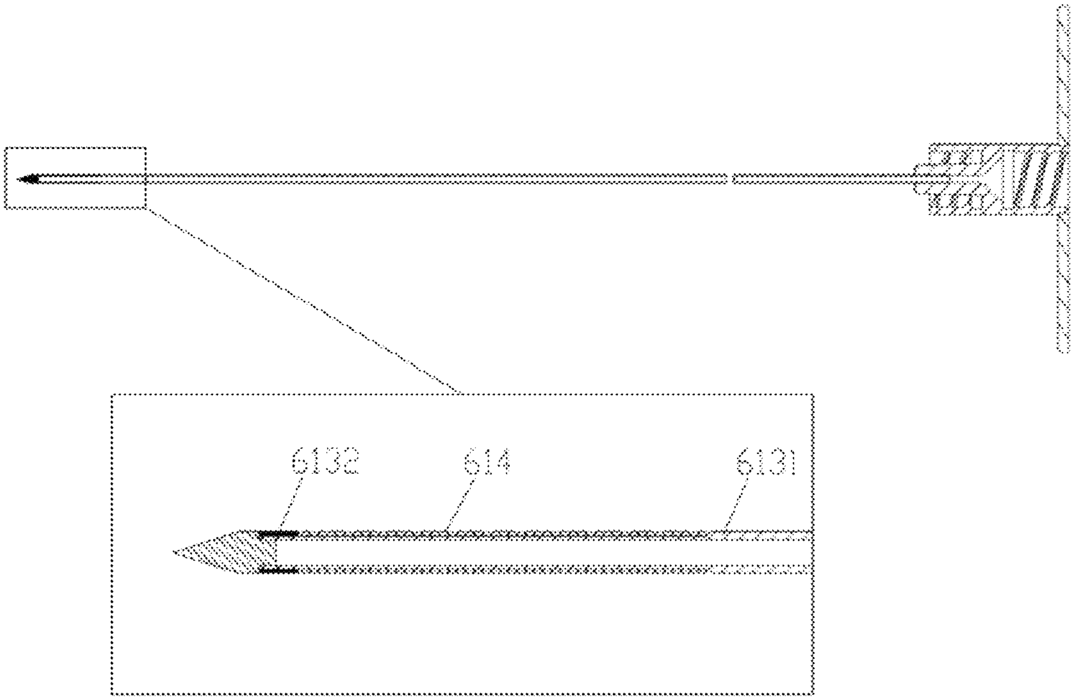
FIG. 19 is a schematic diagram of a puncture needle provided with a spring according to an embodiment of the present disclosure.

FIG. 19 is a schematic diagram of a puncture needle provided with a spring according to an embodiment of the present disclosure. As shown in FIG. 19, in the embodiment of the present disclosure, the inner needle rod 6131 may be a variable-diameter shape, and an outer diameter of a distal portion of the inner needle rod 6131 is smaller than an outer diameter of a proximal portion of the inner needle rod 6131. As shown in FIG. 9, the outer needle rod 6132 and the spring 614 sequentially sleeve at the distal portion of the inner needle rod 6131 from the distal end to the proximal end.

In the embodiment of the present disclosure, the spring may also sleeve on a portion of the inner needle rod 6131 that extends beyond the outer needle rod 6132 in the embodiment of the disclosure as shown in FIG. 16.

The assembly relationship between the sleeve and the needle rod may be the same as the assembly relationship between the spring and the needle rod, as described above.

Figure 20:
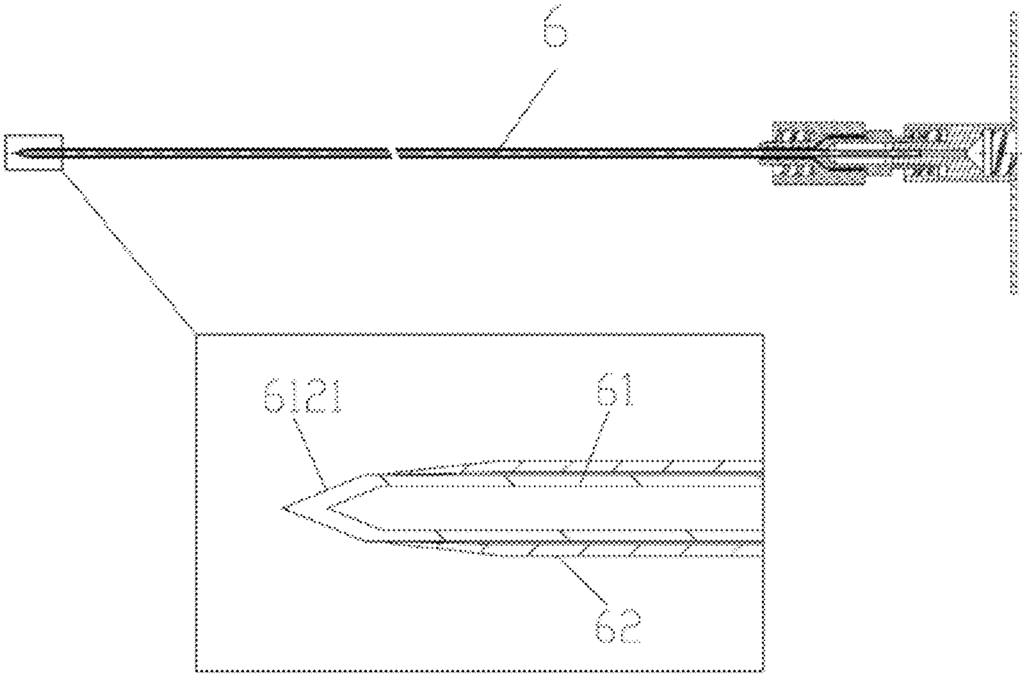
FIG. 20 is a schematic diagram of a puncture needle provided with a catheter according to an embodiment of the present disclosure.

FIG. 20 is a schematic diagram of a puncture needle provided with a catheter according to an embodiment of the present disclosure. As shown in FIG. 20, in the embodiment of the present disclosure, the puncture instrument 6 may include a catheter 62. On one hand, the catheter 62 can be used to establish a channel to transport the guide wire; on the other hand, the catheter 62 can protect the outer surface of the puncture needle 61 to prevent the formation of thrombus and reduce the friction resistance of the puncture needle 61 during movement.

As shown in FIG. 20, the catheter 62 may sleeve outside the puncture needle 61. The distal end of the catheter 62 may be processed by tip molding. After assembly, the distal end of the catheter 62 is located on a proximal side of the conical bottom face of the needle tip 6121 of the puncture needle 61, and the distance between the distal end of the catheter 62 and the conical bottom surface of the needle tip 6121 may be 0 mm to 1 mm, forming interference or transitional fit, exemplarily transitional fit. The proximal end of the catheter 62 may be threaded to the proximal end of the puncture needle 61 by a connector.

Catheterization is widely used in interventional radiology. Most of the catheter instruments used in the past were used to establish the channel for interventional surgical instruments, and most of them did not have the function of specific position bending guidance (Li Yanhao. Diagram of Practical Clinical Interventional Diagnosis and Treatment [M]. Beijing: Science Press, 2012.).

At present, some of the catheter instruments used clinically in human blood vessels and organs need to be bent at a certain angle at a specific position after entering the human body, and guide the interventional surgical instruments such as a puncture needle and a guide wire after bending. For example, the plastic catheter instrument and metal catheter instrument of the RUPS-100 puncture assembly produced by COOK in the United States have a bending and guiding structure at a specific position to achieve the corresponding guiding function.

In the process of intervention, sometimes in order to achieve the guidance of intervention, the distal end of the catheter instrument is required to abut against the interventional target, so that the interventional instrument passes through the catheter instrument and extends beyond the distal end of the catheter instrument, and accurately intervenes at the interventional target.

In order to prevent the distal end of the catheter instrument from causing injury to the tissue when it passed by in the process of passing through the intervention pathway to reach the interventional target, a flexible sleeve may be provided outside the catheter, the flexible sleeve extends beyond the distal end of the catheter, so that the distal end of the catheter is covered by the flexible sleeve to prevent it from harming the surrounding tissues.

In the interventional surgery, especially the interventional surgery with a long and tortuous intervention pathway, the interventional instrument is required to bend at a certain angle in the blood vessel through the catheter instrument before conducting blood vessel or tissue intervention. When the distal end of the flexible sleeve sleeving outside the catheter abuts against the interventional target, due to the flexibility of the flexible sleeve, the flexible sleeve cannot be kept at the interventional target during the intervention process, which often leads to errors such as failure in threading a needle or the change of the intervention direction during the intervention process, resulting in very difficult operation for the surgery implementer. At present, it can only rely on surgical practitioners to extracorporeal catheter support or pressure on specific parts of the human body, which greatly increases the difficulty of operation of the practitioners and limits the application of surgery.

For example, in transjugular intrahepatic puncture surgery, keeping the catheter instrument at the puncture target on the wall of the hepatic vein is the key to the success of the surgical puncture (Li Yanhao. Diagram of Practical Clinical Interventional Diagnosis and Treatment [M]. Beijing: Science Press, 2012.). However, the current puncture assembly cannot effectively solve this problem (Chu Jianguo, Development status and standardization of transjugular intrahepatic portal shunt technique in China, Chin Journal Interventional Radiology (Electronic Edition), 2013, 1 (2)).

Therefore, there is an urgent need for a catheter instrument that can not only prevent damage to the surrounding tissues the catheter instrument passes, but also be kept at the interventional target during the intervention process, so as to prevent errors such as puncture failure in threading a needle or the change of the intervention direction during the intervention process.

Figure 21:
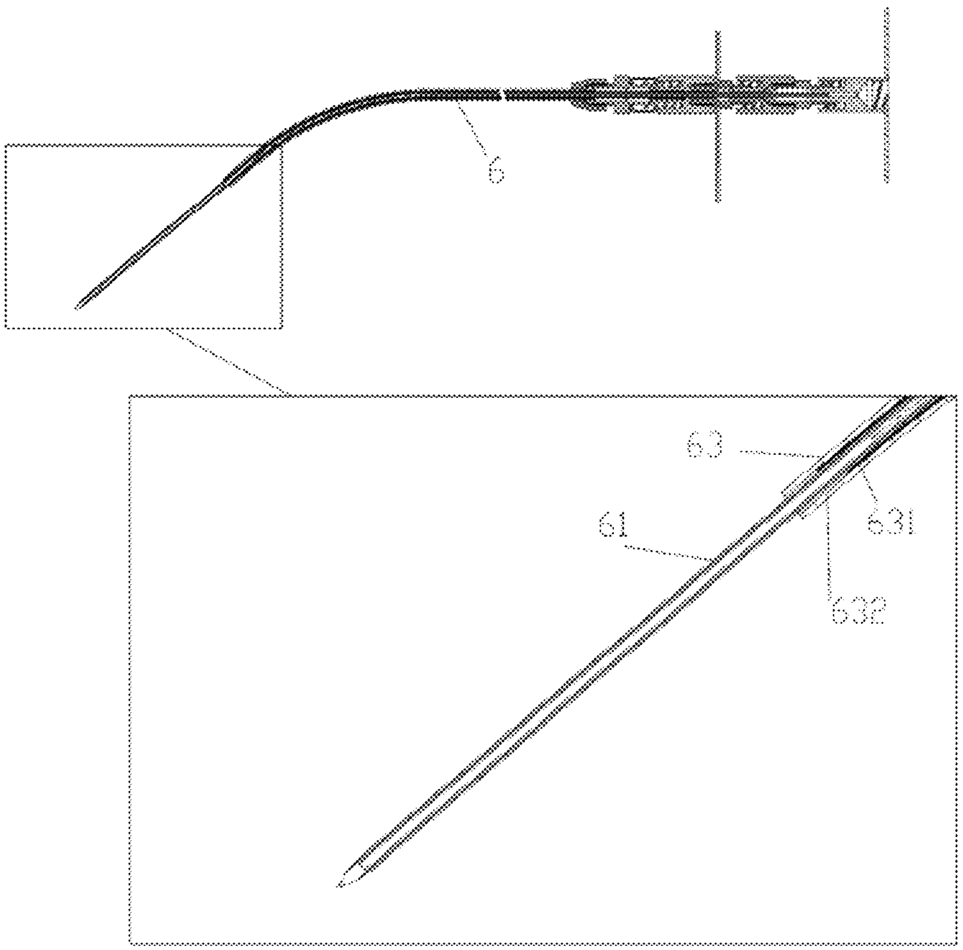
FIG. 21 is a schematic diagram of assembling an interventional catheter instrument and a puncture needle according to an embodiment of the present disclosure.

In the embodiment of the present disclosure, the puncture instrument 6 may include a catheter instrument 63. FIG. 21 is a schematic diagram of assembling an interventional catheter instrument and a puncture needle according to an embodiment of the present disclosure. In the embodiment of the disclosure, as shown in FIG. 21, the catheter instrument 63 may include a guide tube 631 and a flexible sleeve 632, to provide guidance for a puncture needle 61. Depending on clinical needs, the catheter instrument 63 may be linear or curved, and for example, the curved ones may be used in the transjugular intrahepatic puncture surgery.

Figure 22:
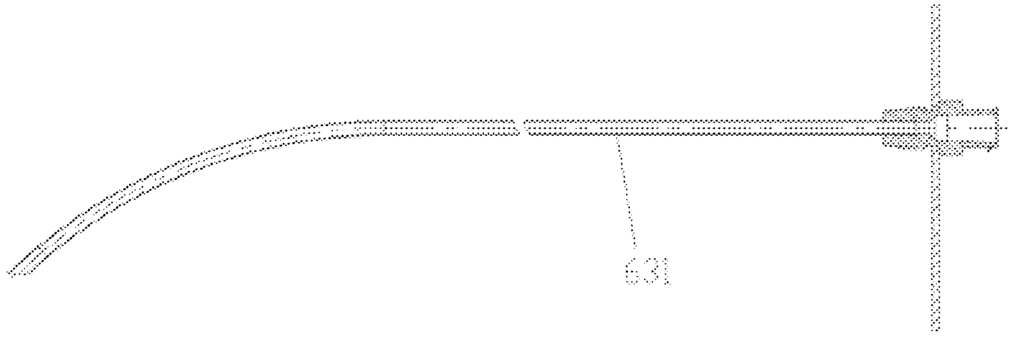
FIG. 22 is a schematic diagram of a guide tube according to an embodiment of the present disclosure.

FIG. 22 is a schematic diagram of a guide tube according to an embodiment of the present disclosure. In the embodiment of the present disclosure, a material of the guide tube 631 may include, but is not limited to, one or more selected from stainless steel, nickel-titanium alloy, etc. Depending on clinical needs, a thickness specification of the guide tube 631 may include, but is not limited to: 13G, 14G, 15G, 16G, etc. (G is the abbreviation of GAUGE, a length metering unit of diameter originating in North America); and a length specification may be 42 cm to 57 cm.

As shown in FIG. 22, the distal end of the guide tube 631 may be of an oblique blade type, which can be used for puncture or for penetrating into the interventional target so as to abut against the interventional target.

As shown in FIG. 22, the distal side of the guide tube 631 may be curved at one or more places according to clinical needs. In an embodiment of the present disclosure, the distal end of the guide tube 631 is of a curved oblique blade type, which may be bent at 10° to 80° at a distance of 0.5 cm to 12 cm from the tip of the oblique blade, for example, may be bent at 60°.

Figure 23:
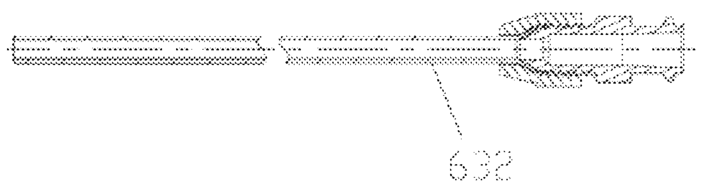
FIG. 23 is a schematic diagram of a flexible sleeve according to an embodiment of the present disclosure.

FIG. 23 is a schematic diagram of a flexible sleeve according to an embodiment of the present disclosure. In the embodiment of the present disclosure, a material of the flexible sleeve 632 may include, but are not limited to, one or more selected from polytetrafluoroethylene (PTFE), fluorinated ethylene propylene copolymer (FEP), thermoplastic polyurethane elastomer (TPU), Polyamide 12 (PA12), Polyether Block Amide (Pebax), high density poly-ethylene (HDPE) and the like.

Figure 24:
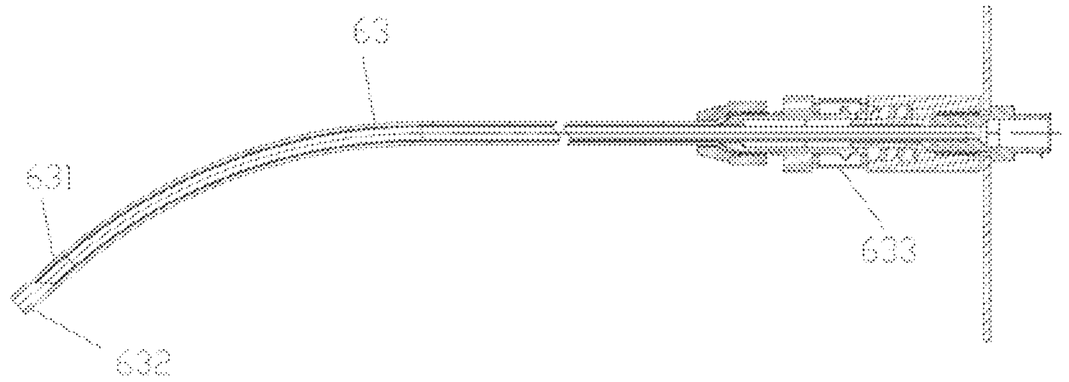
FIG. 24 is a schematic diagram of assembling a guide tube and a flexible sleeve according to an embodiment of the present disclosure.

FIG. 24 is a schematic diagram of assembling a guide tube and a flexible sleeve according to an embodiment of the present disclosure. In the embodiment of the present disclosure, as shown in FIG. 24, the flexible sleeve 632 may sleeve outside the guide tube 631, and its inner diameter is larger than the outer diameter of the guide tube 631 of 0.1 mm to 2 mm. The guide tube 631 and the flexible sleeve 632 may be moved relative to each other so that the distal end of the guide tube 631 may extend beyond the distal end of the flexible sleeve 632, or the distal end of the flexible sleeve 632 may extend beyond the distal end of the guide tube 631 (as shown in FIG. 24).

In the embodiment of the present disclosure, the proximal end of the flexible sleeve 632 may be connected with the proximal end of the guide tube 631 by threading, clasping or bonding through the connector 633, and the flexible sleeve 632 and the guide tube 632 can be moved relatively by the connector 633. As shown in FIG. 21 or 24, the proximal end of the flexible sleeve 632 and the proximal end of the guide tube 631 are connected by threading through the connector 633.

Figure 25:
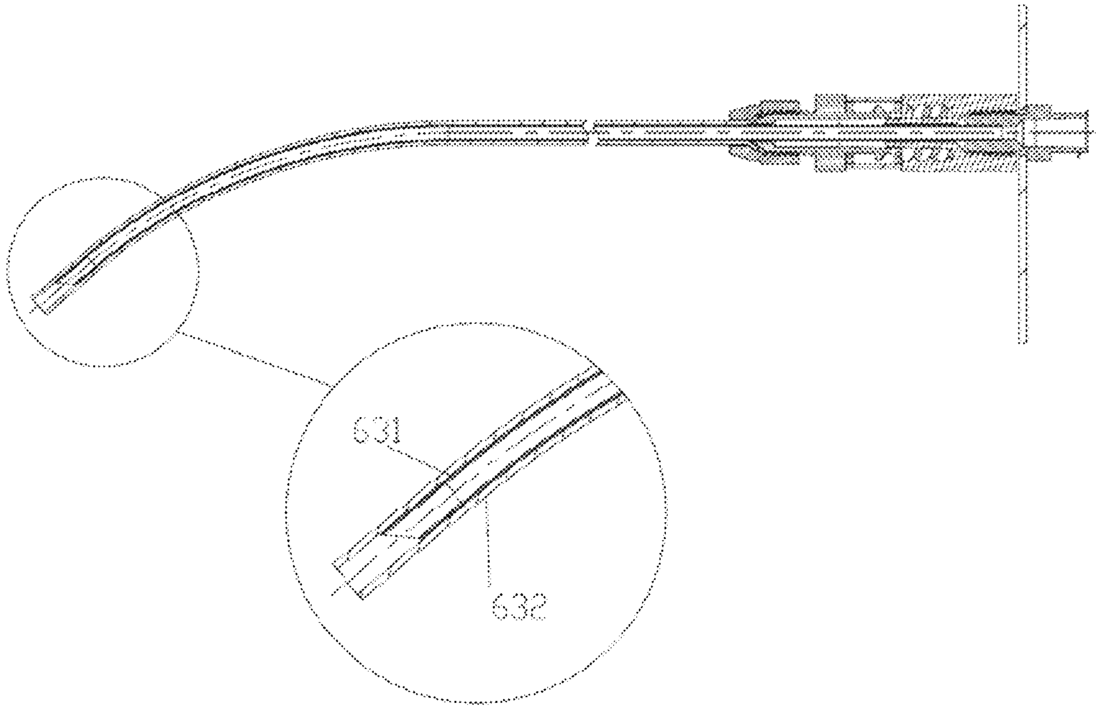
FIG. 25 is a state schematic diagram of the guide tube and flexible sleeve in the process of reaching a puncture target through an intervention pathway according to an embodiment of the present disclosure.

In the puncture surgery according to the embodiment of the present disclosure, the catheter instrument 63 including the guide tube 631 and the flexible sleeve 632 first enters the body via the intervention pathway through the skin or the organ cavity canals or the like to reach the puncture target. FIG. 25 is a state schematic diagram of the guide tube and flexible sleeve in the process of reaching a puncture target through an intervention pathway according to an embodiment of the present disclosure. As shown in FIG. 25, in this process, the flexible sleeve 632 sleeves outside the guide tube 631, and the distal end of the flexible sleeve 632 extends 2 mm to 3 mm beyond the distal oblique blade of the guide tube 631 to prevent the distal oblique blade from harming the tissue passed by.

Figure 26:
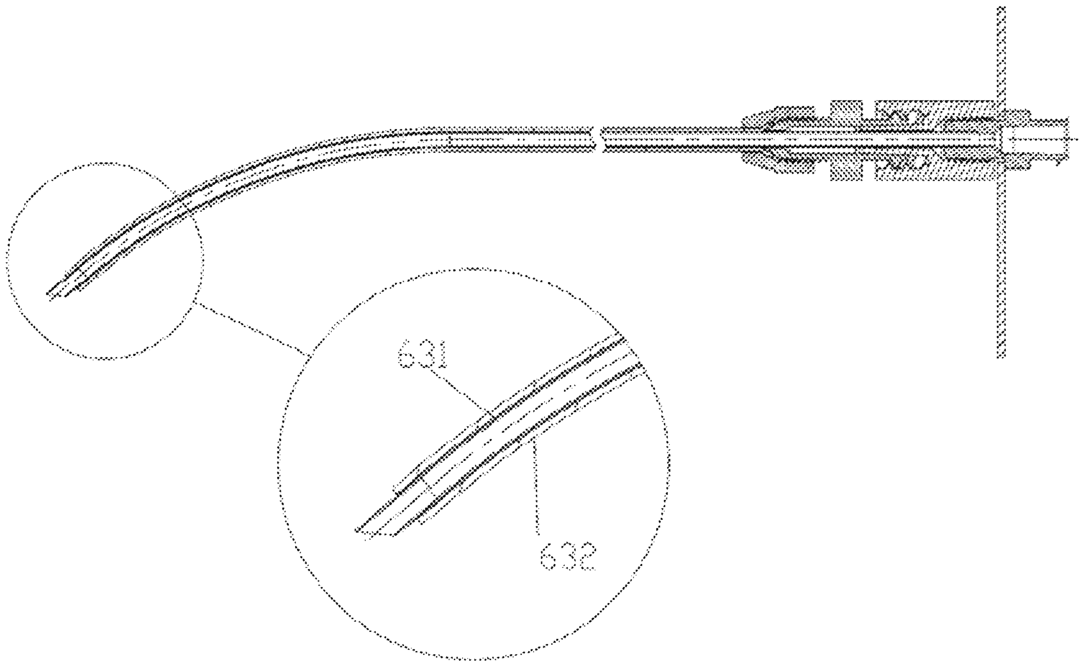
FIG. 26 is a state schematic diagram of the guide tube and the flexible sleeve when implementing puncture guidance according to an embodiment of the present disclosure.

In the puncture surgery according to the embodiment of the present disclosure, when the distal end of the catheter instrument 1 reaches the puncture target, the guide tube 631 and the flexible sleeve 632 can be moved relative to each other, so that the distal end of the guide tube 631 extends beyond the distal end of the flexible sleeve 632, then the distal end of the guide tube 631 can be kept abutting against the puncture target to perform puncture guidance. FIG. 26 is a state schematic diagram of the guide tube and the flexible sleeve when implementing puncture guidance according to an embodiment of the present disclosure.

Figure 27:
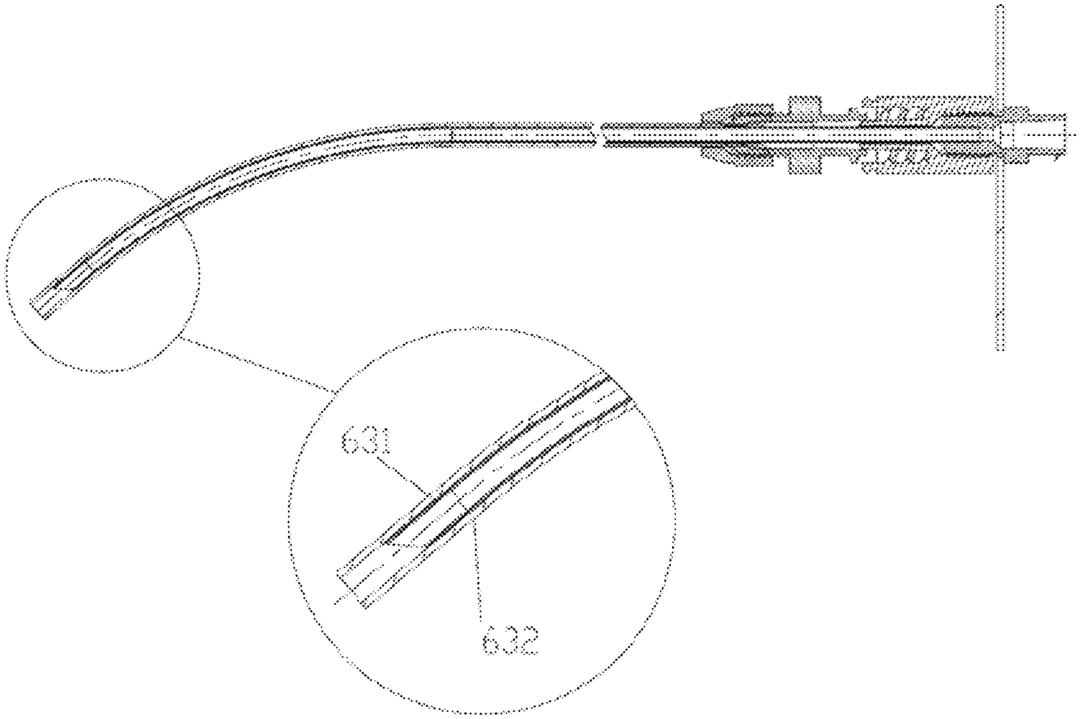
FIG. 27 is a state schematic diagram of the guide tube and flexible sleeve in the process through the intervention pathway after puncture guidance according to an embodiment of the present disclosure.

In the puncture surgery according to the embodiment of the present disclosure, when the catheter instrument 63 is to exit through the intervention pathway after puncture guidance, the guide tube 631 and the flexible sleeve 632 can be moved relative to each other so that the distal end of the flexible sleeve 632 extends beyond the distal oblique blade of the guide tube 631 to prevent the distal oblique blade from harming the tissues passed by. FIG. 27 is a state schematic diagram of the guide tube and flexible sleeve in the exiting process through the intervention pathway after puncture guidance according to an embodiment of the present disclosure.

In the interventional diagnosis and treatment, the distal end of the catheter instrument is subjected to resistance from the tissues and organs it passes by in the process of reaching the interventional target through the intervention pathway, especially in the interventional surgery with a long and tortuous intervention pathway, due to the flexibility of the flexible sleeve, the flexible sleeve often moves to the proximal end relative to the guide tube, so that the distal end of the guide tube extends beyond the distal end of the flexible sleeve, thus damaging the surrounding tissues passed by.

Figure 28:
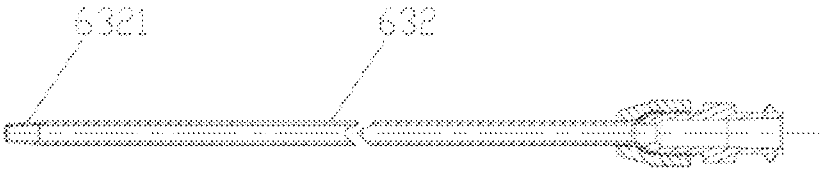
FIG. 28 is a schematic diagram of a flexible sleeve formed by shrinking a distal end according to an embodiment of the present disclosure.

In order to solve the technical problem, further, in the embodiment of the present disclosure, the distal end of the flexible sleeve 632 may be subject to shrinkage molding to form a shrunk portion 6321 which can be conical, and the inner diameter of the shrunk portion after being molded may be smaller than the outer diameter of the guide tube 631 of 0.05 mm to 1 mm. FIG. 28 is a schematic diagram of a flexible sleeve formed by shrinking a distal end according to an embodiment of the present disclosure.

Because the inner diameter of the distal end formed by the shrunk portion of the flexible sleeve 632 is smaller than the outer diameter of the distal end of the guide tube 631, in the process of the catheter instrument 63 reaching the puncture target through the intervention pathway, even if the flexible sleeve 632 is subjected to the resistance from the tissues and organs it passes by, the flexible sleeve 632 will not move to the proximal end relative to the guide tube 631, such that the guide tube 631 will not protrude from the distal end of the flexible sleeve 632, thereby harming the tissues passed by.

Figure 29:
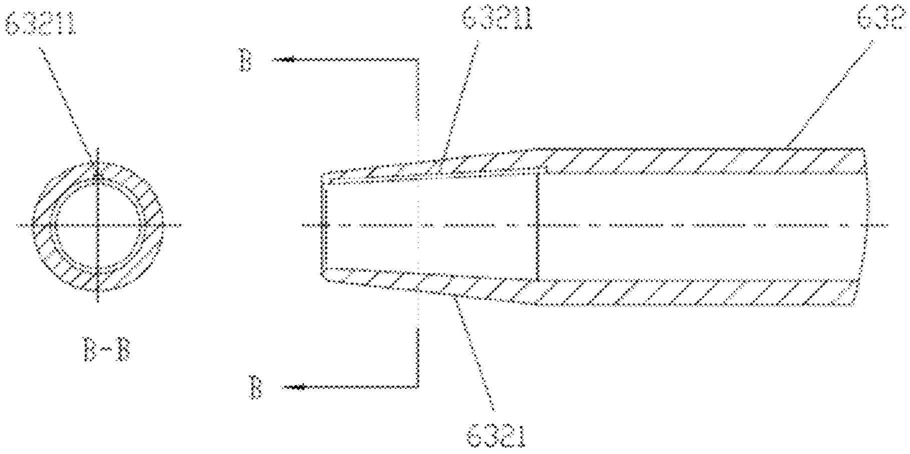
FIG. 29 is a schematic diagram of a shrunk portion of a flexible sleeve according to an embodiment of the present disclosure.

Further, FIG. 29 is a schematic diagram of a shrunk portion of a flexible sleeve according to an embodiment of the present disclosure. In the embodiment of the disclosure, the shrunk portion 6321 of the flexible sleeve 632 may be provided with a weakened portion 63211 which is easy to be damaged, as shown in FIG. 29. The weakened portion 63211 may extend to the distal opening of the flexible sleeve 632. The weakened portion 63211 may be an intermittent indent line or indentation which may extend to the distal opening of the flexible sleeve 632 in a longitudinal direction of the flexible sleeve 632 in a straight manner or helical manner. The weakened portion 63211 may be provided on the inner surface of the shrunk portion 6321 or the outer surface of the shrunk portion 6321. When the weakened portion 63211 is provided on the outer surface of the shrunk portion 6321, a recess may be formed on the outer surface, which may stimulate the blood vessel wall and also affect the blood flow, thus increasing the possibility of thrombosis. Thus, exemplarily, the weakened portion 63211 is provided on the inner surface of the shrunk portion 6321.

The weakened portion 63211 makes it possible for the guide tube 631 to destroy the weakened portion 6321 and to extend out of the distal opening of the flexible sleeve 632, when the catheter instrument 63 abuts against the puncture target and exerts an acting force greater than the above resistance and pushes the guide tube 631 towards the distal end relative to the flexible sleeve 632. In an embodiment of the disclosure, the weakened portion 6321 is a longitudinal indentation with 1 mm wide.

Figure 30:
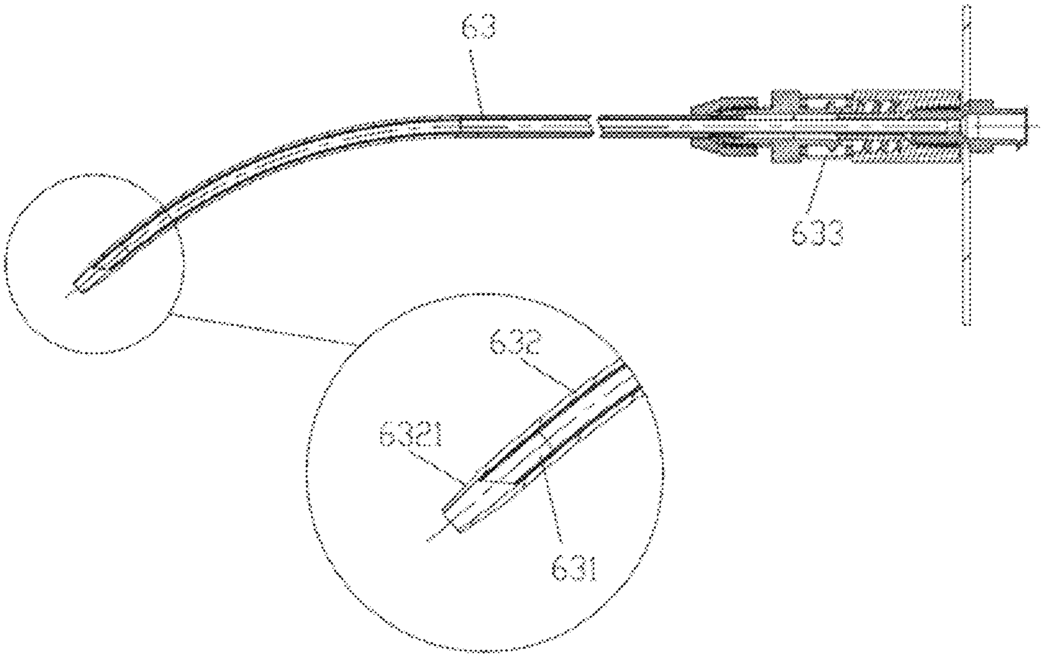
FIG. 30 is a state schematic diagram of the guide tube and flexible sleeve in the process of reaching a puncture target through an intervention pathway according to an embodiment of the present disclosure.

Thus, in the puncture surgery according to the embodiment of the present disclosure, the guide tube 631 and the flexible sleeve 632 first enters the body via the intervention pathway through the skin or organ cavity canals or the like to reach the puncture target. FIG. 30 is a state schematic diagram of the guide tube and flexible sleeve in the process of reaching a puncture target through an intervention pathway according to an embodiment of the present disclosure. As shown in FIG. 30, in this process, the flexible sleeve 632 sleeves outside the guide tube 631, and the shrunk portion of the flexible sleeve 632 extends 2 mm to 3 mm beyond the distal oblique blade of the guide tube 631 to prevent the distal oblique blade from harming the tissue passed by.

Figure 31:
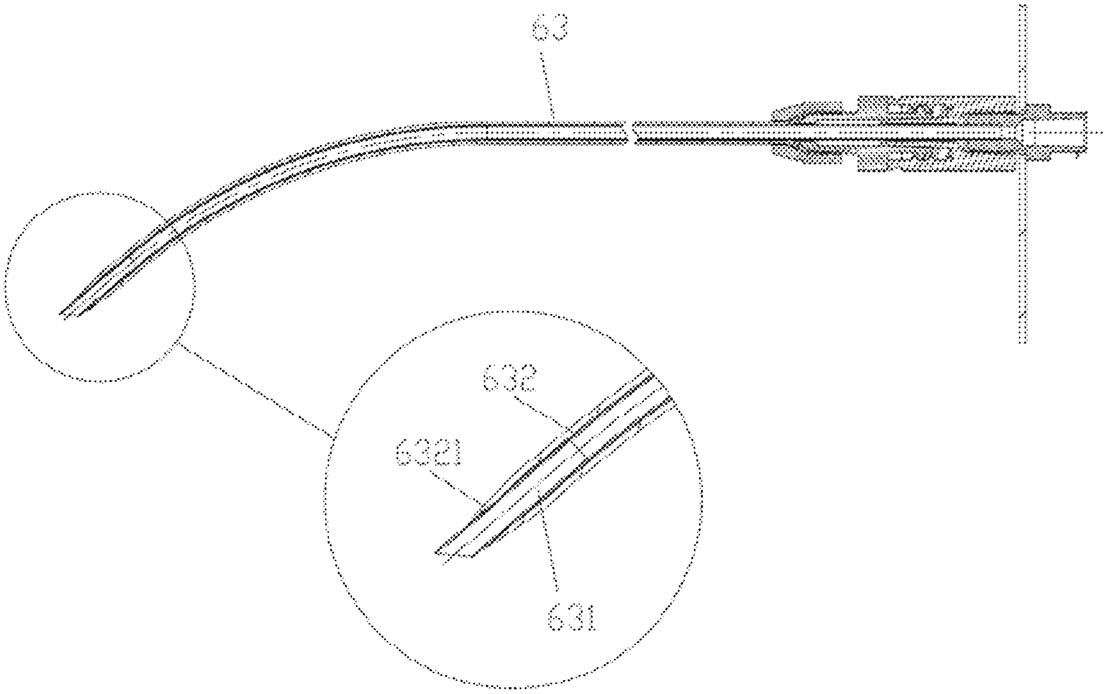
FIG. 31 is a state schematic diagram of the guide tube and the flexible sleeve when implementing puncture guidance according to an embodiment of the present disclosure.

In the puncture surgery according to the embodiment of the present disclosure, when the distal end of the catheter instrument 63 reaches the puncture target, an acting force greater than the above resistance can be exerted and the guide tube 631 can be pushed towards the distal end relative to the flexible sleeve 632, so that the guide tube 631 destroys the weakened portion 6321 and extends 2 mm to 3 mm beyond the distal opening of the flexible sleeve 632. Thus, the distal oblique blade of the guide tube 631 can be penetrated into the puncture target, so that the distal oblique blade can always remain at the puncture target during the puncture process to provide puncture guidance for the puncture needle 61. Then the puncture needle 61 passes through the catheter instrument 63 to puncture to the puncture target. FIG. 31 is a state schematic diagram of the guide tube and the flexible sleeve when implementing puncture guidance according to an embodiment of the present disclosure.

Figure 32:
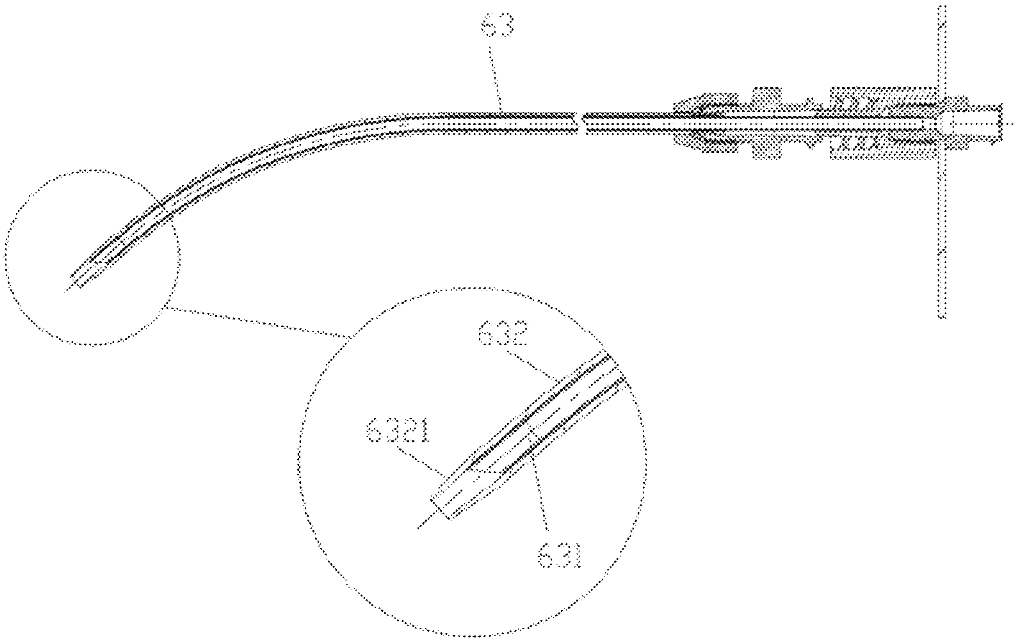
FIG. 32 is a state schematic diagram of the guide tube and flexible sleeve in the exiting process through the intervention pathway after puncture guidance according to an embodiment of the present disclosure.

In the embodiment of the present disclosure, when the puncture by the puncture needle 61 is completed, the guide tube 631 can be pulled back to the proximal end relative to the flexible sleeve 632, so that the distal oblique blade of the guide tube 631 is retracted 3 mm to 5 mm within the distal opening of the flexible sleeve 632. Thereafter, the guide tube 631 and the flexible sleeve 632 are taken out from the original intervention pathway. Since the distal oblique blade of the guide tube 631 has been retracted into the distal opening of the flexible sleeve 632, it will not cause damage to the tissues passed by. In addition, during the withdrawal of the catheter instrument 63, the direction of the resistance exerted on the flexible sleeve 632 is towards the distal end, which will not cause the flexible sleeve 632 to move to the proximal end relative to the guide tube 631, and will not cause the distal end of the guide tube 631 to extend beyond the distal end of the flexible sleeve 632 to cause damage to the tissues passed by. FIG. 32 is a state schematic diagram of the guide tube and flexible sleeve in the exiting process through the intervention pathway after puncture guidance according to an embodiment of the present disclosure.

The interventional catheter instrument according to the embodiment of the disclosure can not only prevent damage to the surrounding tissues the interventional catheter instrument passes, but also be kept at the interventional target in the blood vessel or tissues during the intervention process, so as to build a stable and reliable guiding structure for the surgeon to guide the puncture or insert the interventional instrument. The interventional catheter instrument has the advantages of simple structure and process, low cost, good operability, high efficiency and safety, and can meet the requirements of the surgeons for accurate guidance in curved puncture.

The puncture instrument according to the embodiment of the disclosure can operate a puncture surgery that is easier to operate, more accurate and effective, safer under the interventional navigation technology, thus solving the technical problems existing in the prior art.

The puncture system according to the embodiment of the present disclosure uses interventional navigation technology and corresponding puncture instruments to solve one or more of the above problems of the existing puncture surgery that has a high degree of operation difficulty, poor accuracy and poor safety, susceptibility to complications, and has surgical monitoring blind zones, so as to operate a puncture surgery that is easier to operate, more accurate and effective, safer, and with fewer complications.

In summary, the above embodiments describe the puncture system in detail. Of course, the disclosure includes but is not limited to the above embodiments, and any content transformed on the basis of the above embodiments falls within the scope protected by the disclosure. Those skilled in the art may draw inferences from the contents of the above embodiments.

The above description is only description of a better embodiment of the disclosure, not any limitation to the scope of the disclosure, and any changes and modifications made by those ordinarily skilled in the technical field where the present disclosure belongs according to the above disclosed contents all fall within the scope of protection of the claims.

Although the disclosure is described with reference to the exemplary embodiments, it should be understood that the disclosure is not limited to the specific embodiments described and shown in detail herein, and that those skilled in the art may make various changes to the exemplary embodiments without deviating from the scope defined in the claims, all such changes falling within the scope of protection of the present disclosure.

Those skilled in the art shall understand that, the embodiments of the present disclosure may be provided as a method, a system or a computer program product. Therefore, the present disclosure may be configured with the forms of a full hardware example, a full software example, or combination of a software example and a hardware example. Moreover, the present disclosure may be configured with the form of a computer program product that is implemented on one or more computer-usable storage medium (including but not limited to a disk memory, a CD-ROM, an optical memory, and etc.) including computer-usable program codes.

The present disclosure is described with reference to flow diagrams and/or block diagrams of the method, the device (system) and the computer program product according to the embodiment of the present disclosure. It should be understood that each flow and/or block in the flow diagrams and/or block diagrams, and the combination of the flows and/or blocks in the flow diagrams and/or block diagrams may be implemented by computer program commands. These computer program commands may be provided to a CPU of a general-purpose computer, a special-purpose computer, an embedded processor or other programmable data processing device to produce a machine, so that a device for achieving functions designated in one or more flows in the flow diagrams and/or one or more blocks in the block diagrams can be generated by the command executed by the CPU of the computer or other programmable data processing device.

These computer program instructions may also be stored in a computer-readable memory that can guide a computer or other programmable data processing device to operate in a special way, so that the instruction stored in the computer-readable memory generates a manufactured product including an instruction device, and the instruction device achieves functions designated in one or more flows in the flow diagrams and/or one or more blocks in the block diagrams.

These computer program instructions may also be loaded on a computer or other programmable data processing device, on which a series of operation steps are executed to generate processing achieved by the computer, so that the instruction executed on the computer or other programmable data processing device is provided for being used in the steps of achieving functions designated in one or more flows in the flow diagrams and/or one or more blocks in the block diagrams.

Although exemplary embodiments of the present disclosure have been described, additional changes and modifications may be made to these embodiments once the basic creative concepts are known to those skilled in the art. Accordingly, the attached claims are intended to be construed to include exemplary embodiments and all changes and modifications falling within the scope of the present disclosure.

Obviously, those skilled in the art may make various changes and modifications of the present disclosure without deviating from the spirit and scope of the present disclosure. Thus, if the various equivalent changes or modifications of the present disclosure are made within the scope of the disclosure and the equivalent technology, the present disclosure intends to include the equivalent changes or modifications.

What is claimed is:

1. A puncture system, comprising an interventional navigation system and a puncture instrument; the interventional navigation system comprises an electromagnetic positioning module, a navigation processing module and a navigation output module, wherein, the electromagnetic positioning module is connected with an ultrasonic imaging device and the puncture instrument, configured to obtain position and direction of an ultrasonic image generated by the ultrasonic imaging device and position and direction of the puncture instrument;

the navigation processing module is connected with the ultrasonic imaging device and the electromagnetic positioning module, configured to generate a puncture path based on the position and direction of the puncture instrument, and orthographically project the puncture instrument and the puncture path onto the ultrasonic image to generate a navigation image that fuses a projection of the puncture instrument and the puncture path based on the position and direction of the ultrasonic image, the position and direction of the puncture instrument, and the puncture path; and the navigation output module is connected with the navigation processing module, configured to output the navigation image based on a set display mode, wherein the puncture instrument comprises a puncture needle which comprises a sensor mounting portion, and the sensor mounting portion is capable of mounting a sensor of the electromagnetic positioning module, wherein the sensor mounting portion is an internal cavity of the puncture needle or a concave portion of body surface of the puncture needle, wherein the puncture instrument comprises an interventional catheter instrument, which comprises:

a guide tube; and a flexible sleeve which sleeves outside the guide tube;

wherein the flexible sleeve and the guide tube are capable of moving relatively to each other so that a distal end of the flexible sleeve extends beyond a distal end of the guide tube, or the distal end of the guide tube extends beyond the distal end of the flexible sleeve, wherein the distal end of the flexible sleeve is provided with a shrunk portion, an inner diameter of the shrunk portion is smaller than an outer diameter of the guide tube, and the shrunk portion is provided with a weakened portion which is easy to be damaged; when the interventional catheter instrument abuts against a puncture target, the weakened portion is capable of being destroyed by causing the guide tube to move to the distal end relative to the flexible sleeve, so that the guide tube extends beyond the distal end of the flexible sleeve;

wherein the weakened portion extends to a distal opening of the flexible sleeve; and the weakened portion is provided on an inner surface or an outer surface of the shrunk portion.

2. The puncture system according to claim 1, wherein the puncture needle is tubular, one end of a tubular cavity of the puncture needle is opened at a proximal end of the puncture needle, the other end of the tubular cavity is closed at a distal end of the puncture needle, and the sensor mounting portion is formed by the tubular cavity, wherein the tubular cavity of the puncture needle is the same as the internal cavity of the puncture needle.

3. The puncture system according to claim 2, wherein:

the puncture needle comprises a needle head and a needle rod, and the needle head and the needle rod are connected by welding or threading; and the proximal end of the needle head comprises a connection portion, the needle rod is tubular, and when the needle head is connected with the needle rod, the connection portion is inserted into a tubular cavity of the needle rod, wherein the tubular cavity of the needle rod is the same as the tubular cavity of the puncture needle.

4. The puncture system according to claim 3, wherein an outer diameter of a distal portion of the needle rod is smaller than an outer diameter of a proximal portion of the needle rod.

5. The puncture system according to claim 1, wherein the inner diameter of the shrunk portion is smaller than the outer diameter of the guide tube by 0.05 mm to 1 mm.

6. The puncture system according to claim 1, wherein;

a thickness specification of the guide tube comprises: 13G, 14G, 15G, or 16G, and a length of the guide tube is 42 cm to 57 cm; and an inner diameter of the flexible sleeve is greater than the outer diameter of the guide tube by 0.1 mm to 2 mm.

7. The puncture system according to claim 1, wherein the interventional catheter instrument comprises a connector through which a proximal end of the guide tube is connected with a proximal end of the flexible sleeve, and the guide tube and the flexible sleeve are able to move relative to each other through the connector.

8. The puncture system according to claim 1, wherein the puncture system comprises one of:

when the puncture instrument and the ultrasonic image are in a coplanar state or a non-coplanar state, the navigation image is displayed differently; and when the puncture instrument and the ultrasonic image are in a coplanar state or a non-coplanar state, the projection of the puncture instrument is displayed differently, and/or the projection of the puncture path is displayed differently; and when the puncture instrument and the ultrasonic image are in a non-coplanar state, and an intersection point of the puncture path with the ultrasonic image is displayed differently from other points on the projection of the puncture path; and when the puncture instrument and the ultrasonic image are in a non-coplanar state, projections of two portions of the puncture path on two sides of the ultrasonic image are displayed respectively in different ways, and/or projections of two portions of the puncture instrument on two sides of the ultrasonic image are displayed respectively in different ways.

9. The puncture system according to claim 1, wherein the puncture path in a straight line shape is formed by extending in the direction of the puncture instrument.

10. The puncture system according to claim 1, wherein the electromagnetic positioning module comprises a first sensor connected to a probe of the ultrasonic imaging device, and a second sensor connected to the puncture instrument.

* * * * *